US012749563B2

(12) United States Patent
Constantin

(10) Patent No.: US 12,749,563 B2
(45) Date of Patent: Sep. 29, 2026

(54) ADJUSTING INSULIN THERAPY SETTING BASED ON VARIABILITY OF BLOOD GLUCOSE VALUES

(71) Applicant: Insulet Corporation, Acton, MA (US)

(72) Inventor: Alexandra Elena Constantin, San Jose, CA (US)

(73) Assignee: INSULET CORPORATION, Acton, MA (US)

( * ) Notice: Subject to any disclaimer, the term of this patent is extended or adjusted under 35 U.S.C. 154(b) by 560 days.

(21) Appl. No.: 17/754,737

(22) PCT Filed: Oct. 9, 2020

(86) PCT No.: PCT/US2020/070641
§ 371 (c)(1),
(2) Date: Apr. 11, 2022

(87) PCT Pub. No.: WO2021/072437
PCT Pub. Date: Apr. 15, 2021

(65) Prior Publication Data

US 2023/0037068 A1 Feb. 2, 2023

Related U.S. Application Data

(60) Provisional application No. 62/914,399, filed on Oct. 11, 2019.

(51) Int. Cl.
*G16H 20/17* (2018.01)
*A61M 5/172* (2006.01)

(52) U.S. Cl.
CPC ........... *G16H 20/17* (2018.01); *A61M 5/1723* (2013.01); *A61M 2205/52* (2013.01); *A61M 2230/201* (2013.01)

(58) Field of Classification Search
CPC ................ G16H 20/17; A61M 5/1723; A61M 2230/201; A61M 2230/02
See application file for complete search history.

(56) References Cited

U.S. PATENT DOCUMENTS

2004/0197846 A1* 10/2004 Hockersmith ......... G01N 33/66 435/14
2009/0292190 A1* 11/2009 Miyashita .......... A61B 5/14507 702/19

(Continued)

FOREIGN PATENT DOCUMENTS

WO 2018099912 A1 6/2018
WO WO-2018132723 A1 * 7/2018 .......... A61M 5/1723

OTHER PUBLICATIONS

International Search Report and Written Opinion for PCT Application No. PCT/US2020/070641, mailed on Jan. 27, 2021, 17 pages.

(Continued)

*Primary Examiner* — Fonya M Long
*Assistant Examiner* — Anthony Balaj

(57) ABSTRACT

A method of adjusting insulin therapy settings for a person with diabetes that treats the diabetes by administering first and second types of insulin includes: storing, in a non-transitory storage medium of an electronic device, a first-type insulin dosage suggestion for a person with diabetes regarding a first type of insulin having an active time that is longer than an active time for a second type of insulin; receiving blood glucose data for the person with diabetes, the blood glucose data including blood glucose values for a plurality of days; determining a first variability of the blood glucose values for a selected first period of time during the plurality of days; and modifying the first-type insulin dosage suggestion in the non-transitory storage medium based on the determined first variability.

19 Claims, 18 Drawing Sheets

(56) References Cited

U.S. PATENT DOCUMENTS

| | | | | |
|---|---|---|---|---|
| 2014/0074059 | A1* | 3/2014 | Howell | A61M 5/14244 604/503 |
| 2017/0203037 | A1* | 7/2017 | Desborough | A61B 5/4839 |
| 2017/0329917 | A1* | 11/2017 | McRaith | G16H 50/20 |
| 2018/0154077 | A1* | 6/2018 | Davidson | A61K 38/28 |
| 2019/0147999 | A1* | 5/2019 | Aradottir | G16H 50/20 604/504 |
| 2019/0175833 | A1* | 6/2019 | Sjolund | A61M 5/14244 |
| 2019/0228853 | A1* | 7/2019 | Bengtsson | A61M 5/1723 |
| 2019/0272912 | A1* | 9/2019 | Van Orden | G16H 50/30 |
| 2020/0390973 | A1* | 12/2020 | Wu | G16H 10/40 |

OTHER PUBLICATIONS

Wikipedia: "Area Under the Curve (Pharmacokinetics)", retrieved from internet <https://en.wikipeida.org/w/index.php?title=Area_under_curve_(pharmacokinetics)&oldid=909168455>, May 30, 2006, 3 pages.

Wikipedia: "Statistical Dispersion", retrieved from internet <https://en.wikipedia.org/w/index.php?title=Statistical_dispersion&oldid=900138399>, Jun. 3, 2019, 3 pages.

C. Cobelli et al.: "Diabetes: Models, Signals, and Control," IEEE Reviews in Biomedical Engineering, vol. 2, 2009, pp. 54-96.

Anonymous; "Glycosuria"; Cleveland Clinic Overview; Retrieved from the Internet on Apr. 8, 2025; https://my.clevelandclinic.org/health/diseases/glycosuria; 12 pages.

Chakravarty; "Urine Sugar Test and Normal Blood Sugar in Urine Chart"; Breathe Well-Being; MD Internal Medicine; Nov. 21, 2023, 9 pages.

Anonymous "Urine Glucose Test: Definition and Overview"; Nov. 24, 2009; Retrieved from the Internet on Apr. 8, 2025; https://www.diabetesselfmanagement.com/diabetes-resources/definitions/urine-glucose-test/, 1 page.

* cited by examiner

ADJUSTING INSULIN THERAPY SETTING BASED ON VARIABILITY OF BLOOD GLUCOSE VALUES

CROSS-REFERENCE TO RELATED APPLICATION

This application is a 35 U.S.C. § 371 National Phase Entry Application from PCT Application No. PCT/US2020/070641, filed on Oct. 9, 2020, which claims priority to U.S. Provisional Application No. 62/914,399, filed on Oct. 11, 2019, and entitled "ADJUSTING INSULIN THERAPY SETTING BASED ON VARIABILITY OF BLOOD GLUCOSE VALUES," the entire contents of both of which are incorporated herein by reference.

TECHNICAL FIELD

This document relates to adjusting an insulin therapy setting based at least in part on a variability of blood glucose values.

BACKGROUND

Diabetes mellitus is a chronic metabolic disorder caused by the inability of a person's pancreas to produce sufficient amounts of the hormone insulin such that the person's metabolism is unable to provide for the proper absorption of sugar and starch. This failure leads to hyperglycemia, i.e., the presence of an excessive amount of glucose within the blood plasma. Persistent hyperglycemia has been associated with a variety of serious symptoms and life threatening long-term complications such as dehydration, ketoacidosis, diabetic coma, cardiovascular diseases, chronic renal failure, retinal damage and nerve damages with the risk of amputation of extremities. Because healing is not yet possible, a permanent therapy is necessary which provides constant glycemic control in order to constantly maintain the level of blood analyte within normal limits. Such glycemic control is achieved by regularly supplying external drugs to the body of the patient to thereby reduce the elevated levels of blood analyte. An external biologically effective drug (e.g., insulin or its analog) is commonly administered by means of daily injections. In some cases, multiple, daily injections of a mixture of rapid- and long-acting insulin are administered via a reusable transdermal liquid dosing device.

SUMMARY

In a first aspect, a method of adjusting insulin therapy settings for a person with diabetes that treats the diabetes by administering first and second types of insulin includes: storing, in a non-transitory storage medium of an electronic device, a first-type insulin dosage suggestion for a person with diabetes regarding a first type of insulin having an active time that is longer than an active time for a second type of insulin; receiving blood glucose data for the person with diabetes, the blood glucose data including blood glucose values for a plurality of days; determining a first variability of the blood glucose values for a selected first period of time during the plurality of days; and modifying the first-type insulin dosage suggestion in the non-transitory storage medium based on the determined first variability.

Implementations can include any or all of the following features. The method further comprises: storing, in the non-transitory storage medium, a second-type insulin dosage suggestion for the person with diabetes regarding the second type of insulin; receiving second-type insulin dosage times for the person with diabetes regarding the plurality of days; determining a second variability of the blood glucose values for a selected second period of time during the plurality of days, the second period of time not overlapping the first period of time; and modifying the second-type insulin dosage suggestion in the non-transitory storage medium based on the determined second variability. Determining the first variability comprises determining a measure of dispersion for the blood glucose values for the selected first period of time. Determining the measure of dispersion comprises determining a percentage of the blood glucose values for the selected first period of time that fall below a threshold blood glucose level. Modifying the first-type insulin dosage suggestion comprises: in response to the percentage exceeding a threshold percentage, decreasing the first-type insulin dosage suggestion; and in response to the percentage being less than the threshold percentage, increasing the first-type insulin dosage suggestion. Determining the measure of dispersion comprises evaluating a logarithm-based cost function for the blood glucose values for the selected first period of time. Determining the measure of dispersion comprises determining an area-under-the-curve value for the blood glucose values for the selected first period of time, the area-under-the-curve value determined based on a threshold blood glucose value. Determining the measure of dispersion includes evaluating a mean value of a distribution of the blood glucose values for the selected first period of time, and a standard deviation of the distribution of the blood glucose values for the selected first period of time. Determining the first variability of the blood glucose values comprises evaluating a relationship between a mean value of a distribution of the blood glucose values for the selected first period of time, and a predefined mean value. Evaluating the relationship comprises comparing the predefined mean value to the mean value with a buffer value added to the mean value, and comparing the predefined mean value to the mean value with the buffer value subtracted from the mean value. The first period of time is selected as beginning after a second period of time following a second-type of insulin dosage time during the plurality of days. The method further comprises determining the second-type of insulin dosage time by monitoring a cap sensor of a pen cap, the pen cap configured to fit onto at least a portion of an insulin injection pen. The first period of time is selected as being at least one of fasting time or sleeping time for the person with diabetes. The selected first period of time comprises multiple time segments from the plurality of days that correspond to each other.

In a second aspect, a method of adjusting insulin therapy settings for a person with diabetes that treats the diabetes by administering first and second types of insulin includes: storing, in a non-transitory storage medium of an electronic device, a second-type insulin dosage suggestion for a person with diabetes regarding a second type of insulin having an active time that is shorter than an active time for a first type of insulin; receiving blood glucose data for the person with diabetes, the blood glucose data including blood glucose values for a plurality of days; receiving second-type insulin dosage times for the person with diabetes regarding the plurality of days; determining a first variability of the blood glucose values for a selected first period of time during the plurality of days; and modifying the second-type insulin dosage suggestion in the non-transitory storage medium based on the determined first variability.

Implementations can include any or all of the following features. Determining the first variability comprises determining a measure of dispersion for the blood glucose values for the selected first period of time. The method further comprises: storing, in the non-transitory storage medium, a first-type insulin dosage suggestion for the person with diabetes regarding the first type of insulin; determining a measure of dispersion for the blood glucose values for a selected second period of time during the plurality of days, the second period of time not overlapping the first period of time; and modifying the first-type insulin dosage suggestion in the non-transitory storage medium based on the determined measure of dispersion. The second period of time is selected as beginning after a third period of time following a first-type of insulin dosage time during the plurality of days.

In a third aspect, a diabetes management device includes: a processor; and a non-transitory storage medium having stored therein: a first-type insulin dosage suggestion for a person with diabetes regarding a first type of insulin having an active time that is longer than an active time for a second type of insulin; blood glucose data for the person with diabetes, the blood glucose data including blood glucose values for a plurality of days; and instructions that when executed cause the processor to perform operations comprising: determining a first variability of the blood glucose values for a selected first period of time during the plurality of days; and modifying the first-type insulin dosage suggestion in the non-transitory storage medium based on the determined first variability.

Implementations can include any or all of the following features. The diabetes management device is a pen cap configured to fit onto at least a portion of an insulin injection pen. The diabetes management device further comprises a cap sensor, wherein the first period of time is selected as beginning after a second period of time following a second-type of insulin dosage time during the plurality of days, wherein the operations further comprise: monitoring the cap sensor; and determining the second-type of insulin dosage time based on the monitoring. The diabetes management device is a mobile electronic device. The diabetes management device is a continuous glucose monitor.

BRIEF DESCRIPTION OF DRAWINGS

Like reference symbols in the various drawings indicate like elements.

DETAILED DESCRIPTION

Figure 1:
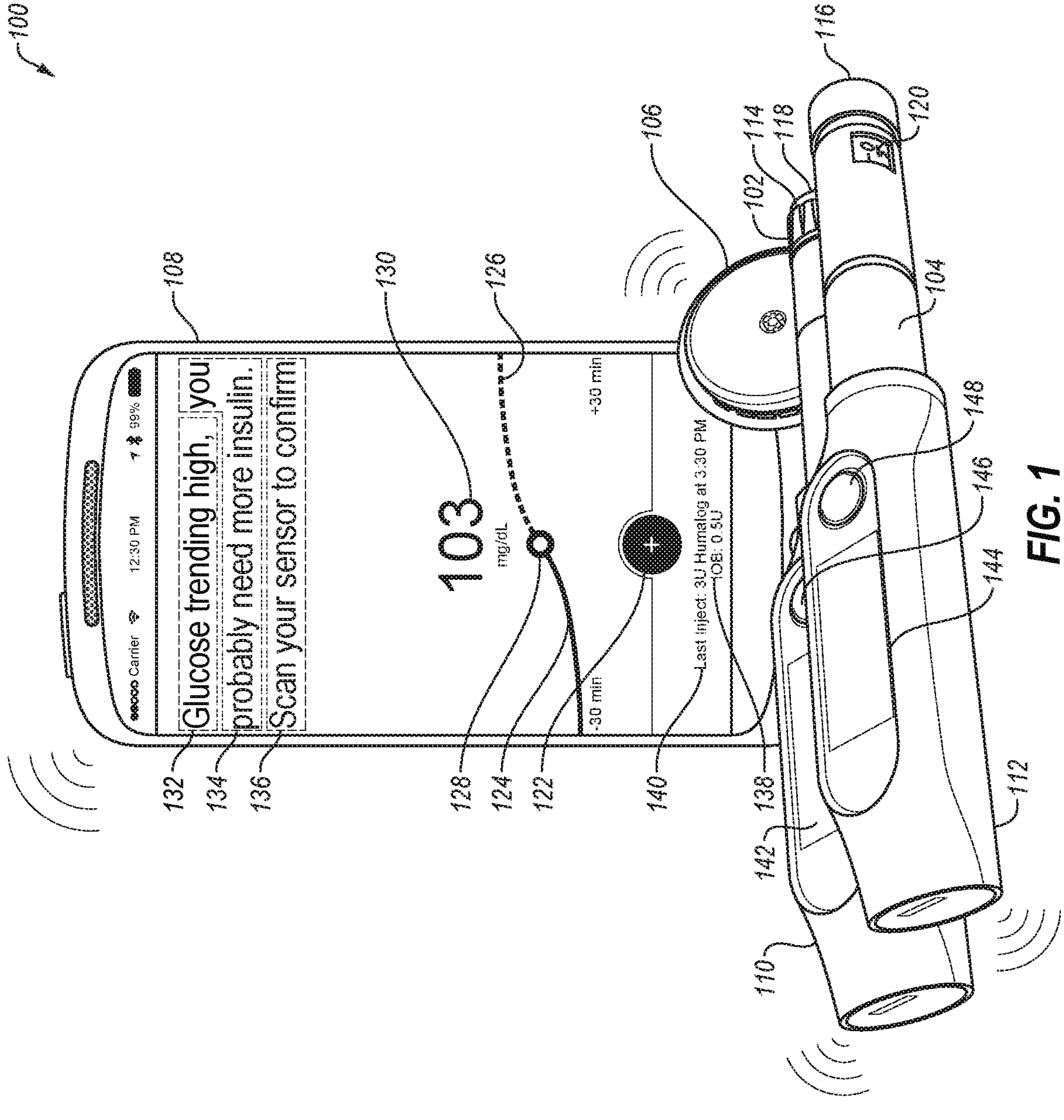
FIG. 1 shows an example of a system for diabetes management.

This document describes examples of systems and techniques for adjusting insulin therapy settings. In some implementations, blood glucose data is collected for a person with diabetes over multiple days, and the blood glucose values of this data can be analyzed by way of isolating one or more relevant time periods of the data. The relevant time period of glucose data can be determined in relationship to the times of insulin dosing. One or more metrics can be applied to a relevant subset of the blood glucose data to determine whether a modification of the insulin therapy is warranted. For example, such an approach can be based on a risk-based variability analysis that results in one or more suggestions being made to the person with diabetes.

Insulin delivery devices include, but are not limited to, insulin injection pens, insulin inhalers, insulin pumps, and insulin syringes. The improper dosing of insulin, whether due to human error, malfunction of an insulin pen, skipping doses, double dosing, or incorrect dosing, is always a concern. Methods, devices, and systems provided herein are described for the delivery of insulin, collection of blood glucose data, and/or the treatment of diabetes. Moreover, methods, devices, and systems provided herein may be adapted for the delivery of other medications, the collection of other analyte data, and/or the treatment of other diseases. Methods, devices, and systems provided herein are described by exemplifying features and functionalities of a number of illustrative embodiments. Other implementations are also possible.

Some examples herein refer to an insulin injection pen. An insulin injection pen includes at least one container holding insulin (e.g., an insulin cartridge), a dial or other mechanism to specify a dose, and a pen needle for transcutaneous delivery of the insulin into the tissue or vasculature of the person with diabetes. In a reusable insulin injection pen, the insulin container (e.g., the cartridge) is replaceable or refillable. A prefilled insulin injection pen is intended for use during a limited time. The dose-specifying mechanism can include a rotatable wheel coupled to mechanics and/or electronics for capping the administered amount of insulin at the volume of the specified dose (e.g., in terms of a number of units of insulin). The dose-specifying mechanism can have a mechanical and/or electronic display that reflects the current setting of the mechanism. The pen needle can be permanently attached to the housing of the insulin injection pen (e.g., as in the case with a disposable pen), or it can be removable (e.g., so that a new needle can be applied when needed). For example, a replaceable pen needle can include a hollow needle affixed to a fitting configured for removeable attachment to an end of the insulin injection pen.

Some examples herein refer to a mobile communication device. As used herein a mobile communication device includes, but is not limited to, a mobile phone, a smartphone, a wearable electronic device (e.g., a smart watch), a tablet, a laptop computer, a portable computer, and similar devices. A mobile communication device includes one or more processors, a non-transitory storage device (e.g., a memory and/or a hard drive) holding executable instructions for operating the mobile communication device, wireless communication components, and one or more input and/or output devices (e.g., a touchscreen, display, or keyboard). The mobile communication device can operate according to one or more application programs stored locally on the mobile communication device, or remotely (e.g., when using cloud computing), or combinations thereof. The mobile communication device can execute at least one operating system in order to perform functions and services.

Some examples herein refer to a continuous glucose monitor (CGM). A CGM is an electronic device configured to take readings of glucose values on an ongoing basis or at regular intervals in order to estimate the blood glucose level of the person with diabetes. Some CGMs determine blood glucose values periodically (e.g., after a certain number of seconds or minutes) and output the information automatically or upon being prompted. The CGM may include wireless communication components for one or more types of signaling, including, but not limited to, Near-Field Communication (NFC) and/or Bluetooth communication.

In some embodiments, systems, devices, and methods provided herein can recommend insulin doses (e.g., dosages of long-acting and/or rapid-acting insulin) using any suitable technique. In some embodiments, recommended insulin dosages may be based upon blood glucose data (e.g., current estimated glucose value (EGV) from a CGM), flash glucose monitor, blood glucose meter, or any other sensor, blood glucose trend data, etc.), insulin administration data (bolus dosage amounts of rapid-acting insulin, dosages of long-acting insulin, dosage times, calculation of Insulin-on-Board ("IOB") and/or active insulin, etc.), meal data (mealtimes, user estimated carbohydrates, user estimated meal categorizations, user estimated glycemic impact of meal user meal history, user meal trends, etc.), and/or one or more insulin deliver parameters total daily dose of basal insulin or long-acting insulin, carbohydrate-to-insulin ratio (CR), insulin sensitivity factor (ISF), etc.). Methods, devices and systems provided herein can, in some embodiments, adjust insulin delivery parameters over time based on glucose data and/or insulin administration data.

Some examples herein refer to long-acting insulin and rapid-acting insulin, or in some cases more generally to first and second types of insulin. Insulin used for therapeutic treatment is often synthesized human insulin. Moreover, different insulins can be characterized in how quickly they typically begin to work in the body of the person with diabetes after administration, and/or how long they typically remain active in the body of the person with diabetes. Rapid-acting insulin can be used to dose for meals or to correct high blood sugar. There is more than one type of insulin that can be considered a rapid-acting insulin. Many, but not necessary all, rapid-acting insulins begin working within about one hour after administration. Similarly, there is more than one type of insulin that can be considered a long-acting insulin, and many, but not necessarily all, long-acting insulins begin working about one hour or longer after administration. Long-acting insulin is often referred to as basal insulin (e.g., insulin used to support basic metabolic needs). Generally, a long-acting insulin has a greater active time (i.e., the length of time that the insulin continues to be active in the body of the person with diabetes after administration) than a rapid-acting insulin. As such, a long-acting insulin is an example of a type of insulin having an active time that is longer than an active time for a type of insulin such as a rapid-acting insulin.

FIG. 1 shows an example of a system 100 for diabetes management. The system 100 can be used in combination with, or can include aspects of, one or more other examples described elsewhere herein. Here, the system 100 includes an insulin injection pen 102. In some implementations, the insulin injection pen 102 is considered an insulin injection pen for a certain type of insulin, such as a rapid-acting insulin pen. For example, the insulin injection pen 102 is a Humalog™ pen, a Novolog™ pen, or an Apidra™ pen. Here, the system 100 includes an insulin injection pen 104. In some implementations, the insulin injection pen 104 is considered an insulin injection pen for a certain other type of insulin having an active time that is longer than an active time for the certain type of insulin, such as a long-acting insulin pen. For example, the insulin injection pen 104 is a Lantus™ pen, a Levemir™ pen, a Toujeo™ pen, or a Tresiba™ pen. Here, the system 100 includes a glucose monitor 106 (e.g., a CGM) or another glucose sensor, and a remote user interface device 108. As shown, each insulin injection pen 102 and 104 includes a corresponding pen cap 110 and 112, respectively, which are in wireless communication with other components of the system 100. As shown, the insulin injection pens 102 and 104 can include dials 114 and 116, respectively, for a user to set a dosage to be delivered, and a respective dose indicator window 118 and 120. In some implementations, one or more of the insulin injection pens 102 and/or 104 may include dose-capture technology and/or be in wireless communication with other components of the system 100. Additional details about possible insulin pens and/or insulin pen caps are exemplified below.

Glucose monitor 106 or another glucose sensor can include any suitable sensor device and/or monitoring system capable of providing data that can be used to estimate one or more blood glucose values. As shown, glucose monitor 106 or another glucose sensor can be a sensor configured to transmit blood glucose data wirelessly. For example, the glucose monitor 106 or another glucose sensor can include an optical communication device, an infrared communication device, a wireless communication device (such as an antenna), and/or chipset (such as a Bluetooth device (e.g., Bluetooth Low Energy (BLE), Classic Bluetooth, etc.), an NFC device, an 802.6 device (e.g., Metropolitan Area Network (MAN), a Zigbee device, etc.), a WiFi device, a WiMax device, a Long Term Evolution (LTE) device, cellular communication facilities, etc.), and/or the like. The glucose monitor 106 or another glucose sensor may exchange data with a network and/or any other devices or systems described in the present disclosure. In some cases, the glucose monitor 106 or another glucose sensor can be interrogated with an NFC device by the user moving one or more components of the system 100 near the glucose monitor 106 or another glucose sensor to power the glucose monitor 106 or another glucose sensor, and/or to transmit blood glucose data from the glucose monitor 106 or another glucose sensor, to other components of system 100. For example, the pen cap 110 and/or 112 can exchange data with (e.g., obtain glucose values from) the glucose monitor 106 or another glucose sensor by being brought in close proximity thereof.

As shown, remote user interface device 108 is a smartphone in some examples. In some implementations, any suitable remote user interface device can be used, including, but not limited to, a computer tablet, a smartphone, a wearable computing device, a smartwatch, a fitness tracker, a laptop computer, a desktop computer, a smart insulin pen (e.g., the pen caps 110 and/or 112), and/or other appropriate computing devices. As shown in the exemplary user interface of the exemplary mobile app running on the depicted smartphone, the user interface can include a bolus calculator button 122 and optionally other buttons for the user to enter data or to request recommendations. The exemplary user interface can also or instead include a display of blood glucose data (e.g., past, present, and/or predicted). As shown, the user interface includes a graph 124 of historical data (e.g., from the previous 30 minutes), a continuation 126 of that graph having projected data, a point indicator 128 showing the current (or most recent) estimated blood glucose value, and a display 130 of the current (or most recent) estimated blood glucose value. The user interface can also or instead include text 132 explaining the glucose data, text 134 and/or text 136 providing suggested actions. For example, text 134 can provide insulin, carbohydrates, or other therapy suggestions. For example, text 136 can suggest that the user obtain blood glucose data. In some cases, the user interface can permit the user to click on the glucose data or otherwise navigate in the mobile app to obtain more detailed or more complete blood glucose data.

The user interface can depict insulin data. In some cases, the user interface can indicate an amount 138 of IOB, which may be only for a particular type of insulin (including, but not limited to, rapid-acting insulin). In some implementations, IOB (sometimes referred to as active insulin) can be defined as the amount of insulin that has been delivered and is still active in the person's body based on estimated duration of insulin action. In some cases, an IOB calculation may be for both rapid-acting and long-acting insulin. In some cases, the user interface can display information 140, including, but not limited to, the time and/or amounts of the most recent doses of quick-acting and/or long-acting insulins. In some cases, the user interface can permit the user to click on the insulin data or otherwise navigate in the mobile app to more detailed and/or more complete insulin delivery data. In some cases, a user interface can overlay blood glucose data and insulin delivery data in any suitable format, such as a graphical display of the timing of blood glucose data vs. the timing of insulin delivery data.

In use, a user (e.g., the person with diabetes and/or a caregiver) can use the system 100 to get recommendations regarding an appropriate insulin dosage. In the case of an upcoming need to deliver long-acting insulin, the text 134 may be changed to provide a recommended long-acting insulin dosage. In some cases, a recommended dosage may appear on pen cap 110 and/or 112. In the case of the user wanting to deliver a bolus of rapid-acting insulin, the user may press bolus calculator button 122 to enter into a bolus calculator. Any suitable bolus calculator could be used in systems, methods, and devices provided herein. For example, the bolus calculator can provide a user interface for a user to enter a meal announcement as either a correction only, a small meal, a normal sized meal, or a large meal. Upon selecting the meal size, the user interface can provide a recommended bolus dosage based on a number of carbohydrates associated with the corresponding button and optionally based upon blood glucose data. Additionally, or alternatively, dose capture pen caps for the insulin injection pen 102 and/or 104 can include a user interface that permits the user to announce a meal size, including, but not limited to, a small meal, medium meal, or large meal.

The pen cap 110 and/or 112 can include at least one display. In some implementations, the pen cap 110 includes a display 142. In some implementations, the pen cap 112 includes a display 144. The display 142 and/or 144 can comprise any suitable type of display technology, including, but not limited to, a dynamic electronic display (e.g., a light-emitting diode display) or a static electronic display (e.g., an E-Ink display). The display 142 and/or 144 can present information to a user, including, but not limited to, any information output that is described elsewhere herein. For example, an insulin dosage suggestion can be presented.

The pen cap 110 and/or 112 can include at least one input control. In some implementations, the pen cap 110 includes a button 146. In some implementations, the pen cap 112 includes a button 148. The button 146 and/or 148 can comprise any suitable type of input technology, including, but not limited to, an electronic switch. The button 146 and/or 148 can trigger the corresponding pen cap 110 and/or 112 to perform one or more operations, including, but not limited to, any operation that is described elsewhere herein.

The pen cap 110 and/or 112 can record and/or convey one or more types of pen capping information. Pen capping information (e.g., information about when the pen cap is secured to and/or released from the injection pen) can include information about a current capping period (e.g., the time since the last capping), information about a duration of one or more uncappings (which may also be referred to herein as "decapping(s)"), and/or the timing (e.g., time-of-day or time elapsed since) of each uncapping and each capping. For example, capping information can include data reflecting when the pen cap was placed onto the insulin injection pen, data reflecting when the pen cap was removed from the insulin injection pen, or both. In some embodiments, pen capping information may be presented to a user on a display of the pen cap. In some embodiments, pen capping information may be presented by a speaker in the pen cap. For example, in some embodiments, a pen cap may provide a timer clock that counts up from the last time the pen cap was secured to the injection pen. In some embodiments, a pen cap accessory can wirelessly communicate pen capping information to a remote computing device (e.g., a smartphone, tablet, etc.). In some embodiments, one or more accessories or smart delivery devices can detect other events associated with medication delivery actions and use that information in ways that pen capping information is described herein. For example, in some cases an injection pen accessory may be secured to an injection pen such that it can detect the mechanical movement of the dosing mechanism to determine a time of a dose of medication.

Pen capping information may be stored, displayed, and/or analyzed in combination with glucose data to determine user behaviors, such as, for example, whether the person is appropriately dosing insulin for meals and/or to correct elevated blood glucose levels. In some embodiments, pen capping information may be presented on a graphical representation of blood glucose data for the user and presented to a user and/or to a healthcare professional. In some embodiments, blood glucose data from a period of time after each capping event may be evaluated to determine whether the user appropriately dosed insulin for that capping event, e.g., appropriate dose, under dose, or over dose.

In some embodiments, a pen capping event may be disregarded where other information indicates that a dose was not provided. For example, where no change in the dosage selection of the insulin pen (e.g., a dial) was detected, the event may be disregarded. In some embodiments, a pen uncapping and recapping event may be disregarded if the total uncapping time is less than a first threshold (e.g., 4-6 seconds). For example, the threshold may be determined by setting it at an amount of time too short to permit for an injection, but long enough to allow a user to check the end of the pen to see if there is insulin remaining or if there is a needle attached to the pen. In some cases, the total decapping time (the time between an uncapping event and the subsequent recapping) for a decapping event may be analyzed in combination with blood glucose data to determine if there was an injection during that decapping event. In some cases, if the total decapping time exceeds a second threshold period of time (e.g., at least 15 minutes, at least 30 minutes, etc.), blood glucose data may be used to determine an approximate time of an injection.

Figure 2A:
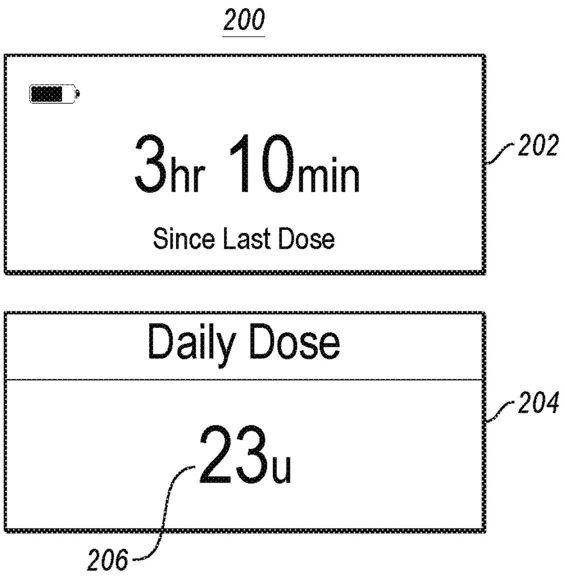
FIGS. 2A-B show examples of graphical user interfaces.
Figure 2B:
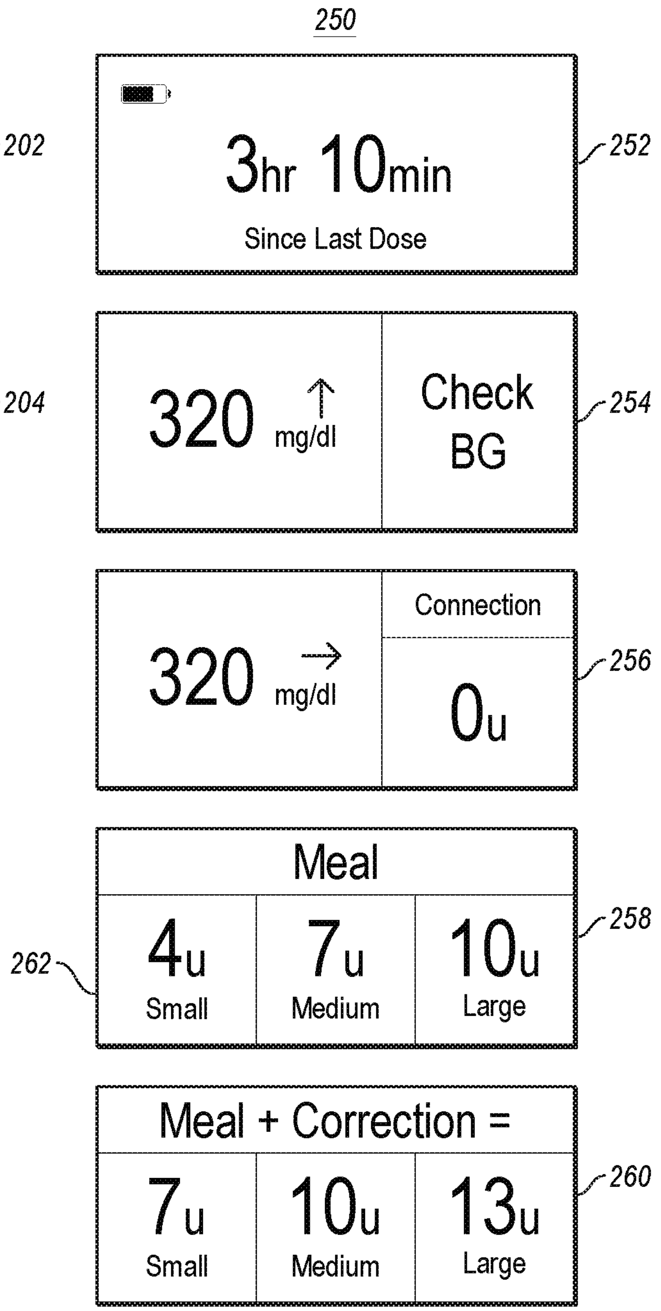

FIGS. 2A-B show examples of graphical user interfaces 200 and 250, respectively. The graphical user interfaces 200 and/or 250 can be used in combination with one or more other examples described elsewhere herein. Each of the graphical user interfaces 200 and 250 can be presented on a suitable display. In some implementations, the graphical user interface 200 relates to an insulin injection pen for a certain type of insulin, such as a long-acting insulin pen. For example, the graphical user interface 200 can be presented on the display 144 of the pen cap 112 (FIG. 1). In some implementations, the graphical user interface 250 relates to an insulin injection pen for a certain other type of insulin, such as a rapid-acting insulin pen. For example, the graphical user interface 250 can be presented on the display 142 of the pen cap 110 (FIG. 1).

One or more of the graphical user interfaces 200 and 250 can support one or more types of processes relating to insulin therapy management. In some implementations, a pairing process can be supported that seeks to establish a connection between the pen cap and one or more other devices. For example, connection between the pen cap and a smartphone (e.g., the remote user interface device 108 in FIG. 1) can be established. In some implementations, a daily use process can be supported that corresponds to the person's with diabetes ordinary use of the pen cap, after one or more successful pairings with the other device(s), to manage diabetes therapy.

In some implementations, a daily use workflow for the graphical user interface 200 can include a default screen (e.g., presenting a name of the insulin currently contained in the insulin injection pen), a timer screen 202, and/or a dose suggestion screen 204. For example, the person with diabetes can cycle through two or more screens using an input control (e.g., the button 148 in FIG. 1). For example, the graphical user interface 200 can automatically return to presenting the default screen if no action is undertaken using the pen cap (e.g., by way of a button other otherwise) within a predefined time period.

In some implementations, the timer screen 202 presents a time that has elapsed since the last dose (e.g., since a most recent capping/uncapping event that qualifies as an indicator of insulin dosage). For example, the timer screen currently states that it has been 3 hours and 10 minutes since the last dose. In some implementations, the elapsed time can be based on actual dosage timing (e.g., as reported by an injection device), or on a proxy for insulin injection timing other than capping/uncapping.

In some implementations, the dose suggestion screen 204 presents an insulin dosage suggestion 206. The insulin dosage suggestion 206 can contain one or more recommendations to the person with diabetes. For example, the insulin dosage suggestion 206 currently suggests that the person with diabetes should ingest a daily dose of insulin (e.g., long-acting insulin) corresponding to an amount of 23 u (units).

In some implementations, a daily use workflow for the graphical user interface 250 can include a default screen (e.g., presenting a name of the insulin currently contained in the insulin injection pen), a timer screen 252, a blood glucose value screen 254, a blood glucose value screen 256, a dose suggestion screen 258, and/or a dose suggestion screen 260. For example, the person with diabetes can cycle through two or more screens using an input control (e.g., the button 146 in FIG. 1). For example, the graphical user interface 250 can automatically return to presenting the default screen if no action is undertaken using the pen cap (e.g., by way of a button other otherwise) within a predefined time period.

In some implementations, the timer screen 252 presents a time that has elapsed since the last dose (e.g., since a most recent capping/uncapping event that qualifies as an indicator of insulin dosage). For example, the timer screen currently states that it has been 3 hours and 10 minutes since the last dose. In some implementations, the elapsed time can be based on actual dosage timing (e.g., as reported by an injection device), or on a proxy for insulin injection timing other than capping/uncapping.

In some implementations, the blood glucose value screens 254 and/or 256 presents data obtained by way of a glucose monitor or another glucose sensor (e.g., a CGM). For example, the blood glucose value screen 254 can present a value of a blood glucose estimate (e.g., 320 mg/dL), present a trend indication (e.g., an arrow pointing up, or towards the right and up, or to the right, or towards the right and down, or down), and/or a suggestion that the person with diabetes should check his or her blood glucose (BG). For example, the blood glucose value screen 256 can present a value of a blood glucose estimate (e.g., 320 mg/dL), present a trend indication (e.g., an arrow pointing up, or towards the right and up, or to the right, or towards the right and down, or down), and an insulin dosage suggestion as to whether the person with diabetes should ingest a correction dose (e.g., here zero units is recommended).

In some implementations, the dose suggestion screen 258 presents an insulin dosage suggestion 262 relating to a meal. The insulin dosage suggestion 262 can contain one or more recommendations to the person with diabetes based on information about the meal. For example, the insulin dosage suggestion 262 currently suggests that the person with diabetes should ingest 4 units of insulin if the meal is a small meal, 7 units if the meal is a medium meal, and 10 units if the meal is a large meal. In some implementations, the pen cap for which the graphical user interface 250 is implemented may work in combination with one or more glucose monitors or another glucose sensor. For example, the graphical user interface 250 can work with a CGM. As another example, the graphical user interface 250 can work with a blood glucose meter.

The graphical user interface 200 and/or 250 can present one or more other types of information not illustrated in the present examples. Such information can include, but is not limited to, messages regarding a need to charge the pen cap, messages that the pen cap is currently synchronizing data, and/or error messages (e.g., urging the person with diabetes to consult the remote user interface device 108 (FIG. 1).

Figure 3:
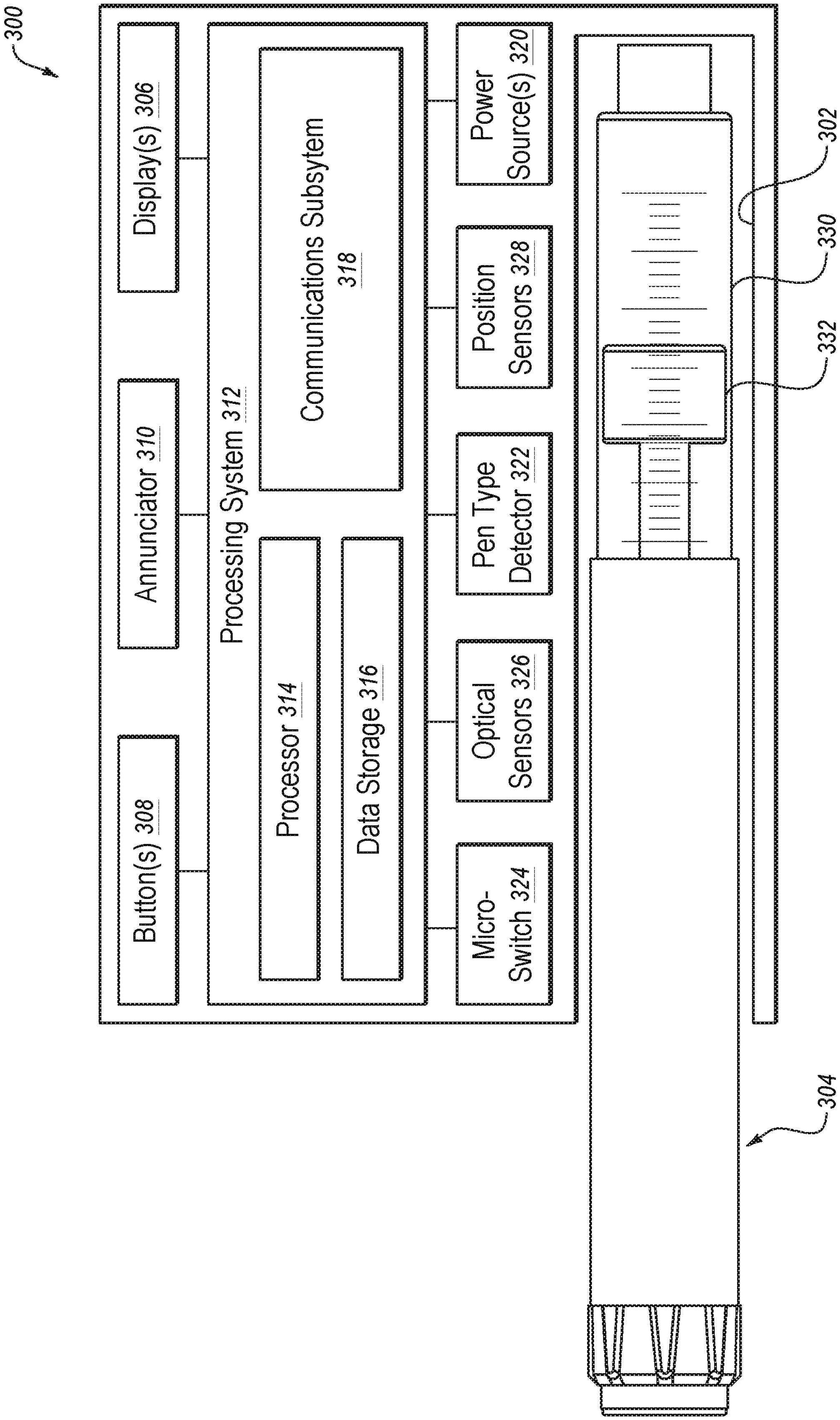
FIG. 3 shows an example schematic of internal components of a pen cap for an insulin injection pen.
Figure 4A:
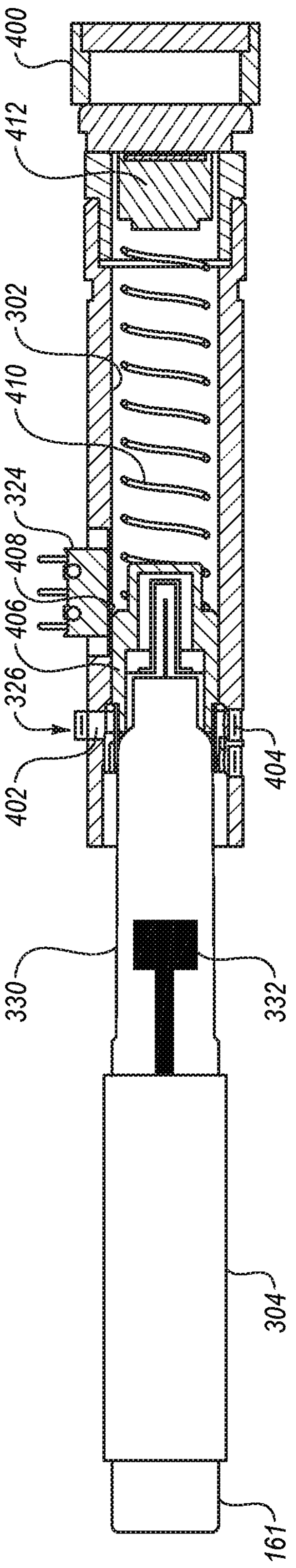
FIGS. 4A-B show examples of a pen cap for an insulin injection pen.
Figure 4B:
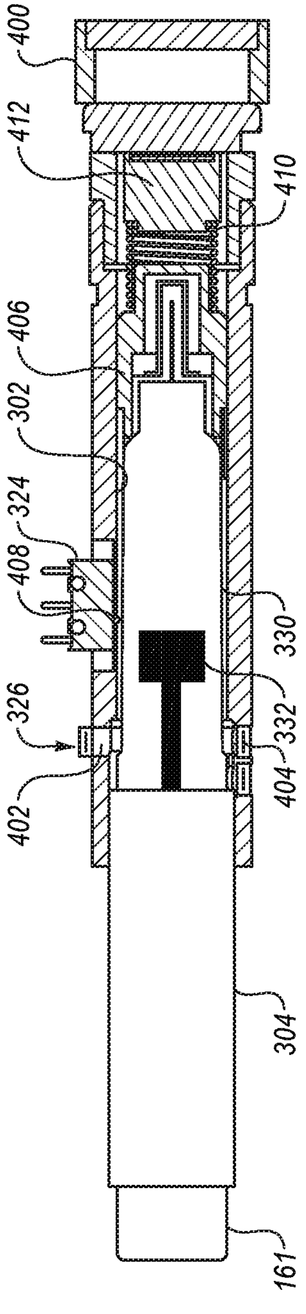

FIG. 3 shows an example schematic of internal components of a pen cap 300 for an insulin injection pen. FIGS. 4A-B show examples of a pen cap 400 for an insulin injection pen. The pen cap 300 and/or the pen cap 400 can be used in combination with, or can include aspects of, one or more other examples described elsewhere herein.

The pen cap 300 includes a cavity 302 that is configured to accommodate at least a portion of an insulin injection pen 304 (e.g., the insulin injection pen 102 and/or 104 of FIG. 1). For example, the cavity 302 can facilitate that the pen cap 300 has the ability to fit onto at least a portion of the insulin injection pen 304 (e.g., the portion thereof having a needle). As shown, the pen cap 300 can include one or more displays 306, one or more buttons 308, and one or more annunciator (s) 310, each controlled by a processing system 312. Processing system 312 includes a processor 314, data storage (or memory) 316, and a communications subsystem 318. The communications subsystem 318 can enable wireless communication between the pen cap and a remote user interface device (e.g., the remote user interface device 108 of FIG. 1) or a glucose sensor or monitor (e.g., the glucose monitor 106 of FIG. 1, or another glucose sensor). In some cases, the communications subsystem 318 can include an NFC chip or chipset. In some cases, the communications subsystem 318 can include a BLE chip or chipset. In some cases, the communications subsystem 318 can include an optical communication device, an infrared communication device, a wireless communication device (such as an antenna), and/or a chipset (an 802.6 device (e.g., MAN, a Zigbee device, etc.), a WiFi device, a WiMax device, an LTE device, cellular communication facilities, etc.), and/or the like. In these and/or other cases, the communications subsystem 318 can exchange data with a network and/or any other device or system (e.g., as described in the present disclosure). The pen cap 300 includes a power source 320, which may be a rechargeable or non-rechargeable battery. The processing system can determine a pen type from data from a pen type detector 322. The processing system 312 can determine the presence or the absence of the insulin injection pen 304 from the cavity 302. The processing system 312 can determine a position of a plunger within the insulin injection pen 304 using one or more optical or position sensors and/or micro switches, such as micro switch 324, optical sensor(s) 326, and position sensor(s) 328. The insulin injection pen 304 includes an insulin vial 330 and a plunger 332.

FIGS. 4A-B illustrate examples of arrangements of the position sensor 328, micro switch 324, and optical sensor 326 of FIG. 3 within the pen cap 400. The optical sensor 326 can include a light 402 and photoreceptor 404 positioned on opposite sides of the insulin injection pen 304 so that light passes through the insulin vial 330 and is received by the photoreceptor 404 until the plunger 332 of the insulin injection pen 304 passes by the optical sensor 326. The tip of insulin injection pen 304 is received by a slider 406 that slides within the pen cap 400 to trigger the micro switch 324, here including trigger 408 to instruct or trigger the pen cap 400 to use the optical sensor 326 to identify when the plunger 332 passes the optical sensor 326. Data from position sensor 328, which here includes spring 410, slider 406, and proximity sensor 412, can be used to determine the distance that the insulin injection pen 304 is inserted into the pen cap 400 by the time the plunger 332 passes the optical sensor 326. Thus, it can be determined an amount of insulin remaining in the insulin vial 330. Data from prior use of the pen cap 400 can then be used to estimate an amount of insulin delivered to the patient.

Figure 5:
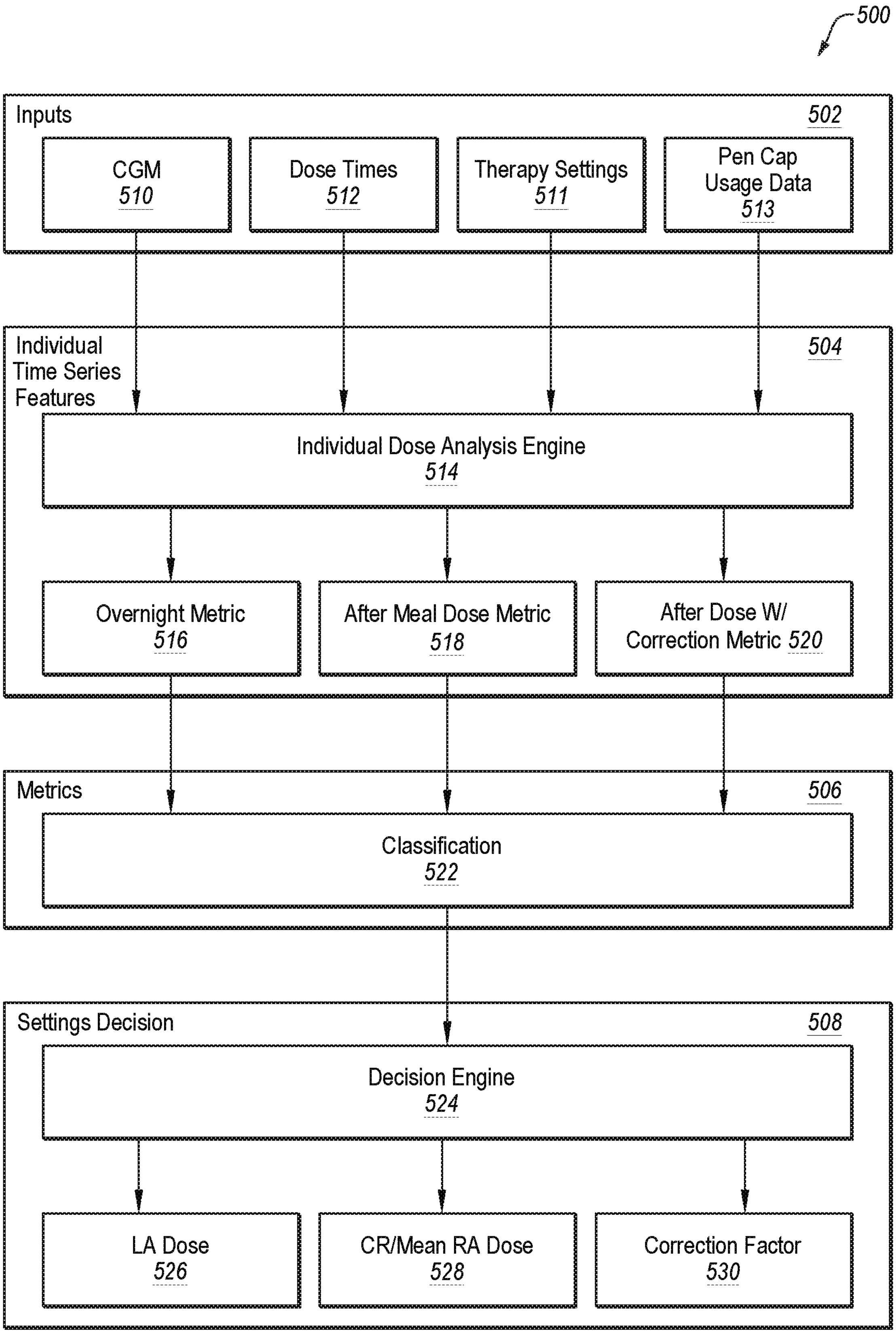
FIG. 5 shows a diagram of an example system for diabetes management.

FIG. 5 shows a diagram of an example system 500 for diabetes management. The system 500 can be used in combination with, or can include aspects of, one or more other examples described elsewhere herein. The system 500, or one or more components thereof, can be implemented using one or more components exemplified below in the description of FIG. 14.

The system 500 can include an inputs layer 502, an individual time series features layer 504, a metrics layer 506 for determining the mean and variability for specific time series features, and a settings decision layer 508. The inputs layer 502 can facilitate that the system 500 obtains data regarding blood glucose levels and/or dosage times. In some implementations, the inputs layer 502 facilitates connection with a CGM 510 (e.g., the glucose monitor 106 of FIG. 1, or another glucose sensor). In some implementations, the inputs layer 502 facilitates receipt of therapy settings 511. For example, the therapy settings 511 specifies one or more doses of insulin, and/or characteristics of the dose(s) of insulin, for a person with diabetes. In some implementations, the inputs layer 502 facilitates receipt of dose times data 512 (e.g., by way of detecting capping data from a pen cap of an insulin injection pen, or using another proxy for dosage times). In some implementations, the inputs layer 502 facilitates receipt of pen cap usage data 513. For example, the pen cap usage data 513 can be based on one or more capping or uncapping event of a pen cap for an insulin injection pen. One or more of the CGM 510, therapy settings 511, dose times data 512, or the pen cap usage data 513 can be used in some implementations. For example, the dose times data 512 can be determined or inferred from the pen cap usage data 513. In some implementations, the inputs layer 502 can receive about two weeks of blood glucose data and dosage timing information. In some implementations, the time period between therapy parameter adjustments can be configurable by an algorithm. For example, the time period between consecutive therapy parameter adjustments can be referred to as an iteration of the algorithm. The inputs layer 502 can provide some or all of the information to the individual features/metrics layer 504.

The individual time series features layer 504 can serve to select the relevant data features that will help with the evaluation of success or lack thereof of each insulin dose. For example, such insulin doses can include rapid-acting insulin doses and/or long-acting insulin doses. In some implementations, the individual time series features layer 504 includes an individual dose analysis engine 514. For example, the individual dose analysis engine 514 can identify one or more individual dose times in dose times data 512, identify one or more blood glucose values from the CGM 510 corresponding to the identified one or more individual dose times, calculate one or more other metrics such as mu* or sigma* from a set of time series features of interest, and/or compare the identified one or more blood glucose values to one or more applicable blood glucose threshold values (e.g., a low blood glucose threshold).

The individual dose analysis engine 514 can select one or more metrics to be applied in analyzing sets of individual dose outcomes. In some implementations, the individual dose analysis engine 514 applies one or more of a metric 516 relating to overnight insulin dosage, a metric 518 relating to insulin dosage taken after a meal, and/or a metric 520 relating to an after-meal dose with a correction dose. For example, the metric 516 can be applied to a portion of the blood glucose data that can correspond to sleeping time for the person with diabetes (e.g., sleeping time can be an example of fasting time for the person with diabetes). For example, the metric 518 can be applied to a portion of the blood glucose data that corresponds to time in connection with an ingested meal. For example, the metric 520 can be applied to a portion of the blood glucose data that corresponds to time in connection with an eaten meal, wherein the dose times data 512 indicates that the person with diabetes took a correction dose (e.g., an insulin dosage suggestion made to the person with diabetes may have included a correction bolus recommendation, and capping data from the pen cap indicates that the correction bolus recommendation was accepted by the person with diabetes.)

In the metrics layer 506, one or more of the metrics selected by the individual dose analysis engine 514 can be applied to determine a variability. The application of at least one metric to a portion of data can be referred to as determining a variability of values (e.g., blood glucose values) within that data. In some implementations, the metrics layer 506 includes a classification component 522 that classifies one or more instances of blood glucose data, and/or one or more insulin dosages, using the selected metric(s). For example, the classification component 522 can apply the metric(s) to blood glucose data to determine whether a particular insulin therapy (e.g., as manifest by one or more insulin dosage suggestions made to the person with diabetes) was successful.

The settings decision layer 508 can make one or more decisions based on the variability determined by the metrics layer 506. In some implementations, the settings decision layer 508 includes a decision engine 524. For example, the decision engine 524 can evaluate the variability determined by the metrics layer 506 and decide that one or more modifications should be made to an insulin dosage recommendation.

The decision made by the settings decision layer 508 can result in one or more suggestions being modified. In some implementations, at least one insulin dosage suggestion may be stored (e.g., in a memory or other non-transitory storage medium) and associated with a particular person with diabetes. The insulin storage suggestion can be stored in a device associated with the person with diabetes, including, but not limited to, in a pen cap, a smartphone, and/or a CGM. Based on the operations of the inputs layer 502, the individual time series features layer 504, the metrics layer 506, and the settings decision layer 508, one or more stored insulin dosage suggestions can be modified (in the memory or other non-transitory storage medium). For example, an insulin dosage suggestion can be increased or decreased. Here, the decision engine 524 can access, and is able to modify or otherwise update, a long-acting (LA) dose suggestion 526, a rapid-acting (RA) dose suggestion 528 relating to a CR or the mean of a blood glucose distribution, and/or a correction factor suggestion 530. That is, after one or more of the long-acting dose suggestion 526, rapid-acting dose suggestion 528, and/or correction factor suggestion 530 is modified, the next time a suggestion of the corresponding type is to be made to the person with diabetes, the modified suggestion can be accessed in the memory or other non-transitory storage medium and used to make an output to the person with diabetes accordingly.

Use of the system 500 illustrates an example of a method of adjusting insulin therapy settings for a person with diabetes. Particularly, insulin therapy settings may relate to the situation where the person with diabetes treats the diabetes by administering first and second types of insulin (e.g., long-acting and rapid-acting insulin, respectively). That is, there may be at least an insulin dosage suggestion for the first type of insulin, here referred to as a first-type insulin dosage suggestion, and the method may include storing the first-type insulin dosage suggestion in a non-transitory storage medium of an electronic device (e.g., a pen cap, a smartphone, and/or a CGM). The long-acting dose suggestion 526 can be stored by the system 500. In some implementations, the first-type insulin dosage suggestion can include the insulin dosage suggestion 206 (FIG. 2A). For example, the first-type insulin dosage suggestion can relate to the daily dose of long-acting insulin.

The method may include receiving blood glucose data for the person with diabetes, and such blood glucose data can include blood glucose values for a plurality of days. For example, the CGM 510 can include blood glucose values (e.g., for a plurality of days) and the dose times data 512 can indicate (estimated) dosage times during the time interval of the blood glucose values.

The method may include determining a first variability of the blood glucose values for a selected period of time during the plurality of days. In some implementations, the plurality of days can include a time longer than one week, including, but not limited to about two weeks' worth of blood glucose data. In some implementations, the plurality of days can include a time shorter than one week. The selected period of time can be one or more continuous sections of time during the plurality of days. The selected period of time is chosen so as to exclude one or more time periods from a variability determination. In some implementations, the period of time is selected so as to represent a duration of time during which the blood glucose effects of the most recently ingested meal are negligible or no longer significant. Generally, such a time can be referred to as a fasting time for the person with diabetes. Fasting time includes, but is not limited to, time during the period when the person with diabetes sleeps. In some implementations, the time of sleep can be defined in the data as occurring during the longest time elapsed between consecutive insulin doses. For example, the time can be defined as beginning at the earlier of the two doses and extending for about 4-6 hours. For this reason, the selected time period may be referred to as fasting time (e.g., sleeping time) for the person with diabetes. For example, the first variability can be determined for a fasting period that includes a number of hours when the person with diabetes is asleep.

The method can include modifying the first-type insulin dosage suggestion in the non-transitory storage medium based on the determined first variability. For example, if the determined first variability indicates that the insulin ingested by the person with diabetes in relation to the selected period of time led to an undesirable blood glucose level during at least part of the selected period of time, then the first-type insulin dosage suggestion can be adjusted accordingly.

The just described example illustrates modification of the first-type insulin dosage suggestion. In some implementations, there may be at least an insulin dosage suggestion also for the second type of insulin, here referred to as a second-type insulin dosage suggestion (e.g., the meal suggestion on the dose suggestion screen 258 in FIG. 2B). The second-type insulin dosage suggestion may also or instead be modified. In such a method, the method may include storing the second-type insulin dosage suggestion in the non-transitory storage medium. The method may include receiving second-type insulin dosage times for the person with diabetes regarding the plurality of days. That is, the second-type insulin dosage times can indicate (or estimate) when the person with diabetes has ingested the second type of insulin during the plurality of days. For example, the dose times data 512 may include such information (e.g., based on capping events of a pen cap associated with an insulin injection pen).

The method may include determining a second variability of the blood glucose values for a selected second period of time during the plurality of days, the second period of time not overlapping the first period of time. In some implementations, the second period of time is associated with a meal ingested by the person with diabetes (e.g., the second time period starts at the time of the meal and extends for a specific number of hours thereafter.) The first period of time, moreover, can be defined or selected so as to follow after the second period of time, without overlap. For example, this can seek to ensure that the first period of time, which perhaps is intended to be a fasting period of time, follows sufficiently long after the most recent meal.

The method may include modifying the second-type insulin dosage suggestion in the non-transitory storage medium based on the determined second variability. For example, if the determined second variability indicates that the insulin ingested by the person with diabetes in relation to the selected period of time led to an undesirable blood glucose level during at least part of the selected period of time, then the second-type insulin dosage suggestion can be modified accordingly.

In some implementations, a second-type insulin dosage suggestion can be modified with or without modification of a first-type insulin dosage suggestion (e.g., there may or may not exist any first-type insulin dosage suggestion in the system). Use of the system 500 illustrates an example of a method of adjusting insulin therapy settings in such a scenario.

The method may include storing, in a non-transitory storage medium of an electronic device, a second-type insulin dosage suggestion for a person with diabetes regarding a second type of insulin having an active time that is shorter than an active time for a first type of insulin. For example, the meal suggestion on the dose suggestion screen 258 in FIG. 2B can be stored.

The method may include receiving blood glucose data for the person with diabetes, the blood glucose data including blood glucose values for a plurality of days. For example, the CGM 510 can include blood glucose values (e.g., for a plurality of days) and the dose times data 512 can indicate (estimated) dosage times during the time interval of the blood glucose values.

The method may include receiving second-type insulin dosage times for the person with diabetes regarding the plurality of days. That is, the second-type insulin dosage times can indicate (or estimate) when the person with diabetes has ingested the second type of insulin during the plurality of days. For example, the dose times data 512 may include such information (e.g., based on capping events of a pen cap associated with an insulin injection pen).

The method may include determining a first variability of the blood glucose values for a selected first period of time during the plurality of days. In some implementations, the first period of time is associated with a meal ingested by the person with diabetes (e.g., the first time period starts at the time of the meal and extends for a specific number of hours thereafter.)

The method may include modifying the second-type insulin dosage suggestion in the non-transitory storage medium based on the determined first variability. For example, if the determined first variability indicates that the insulin ingested by the person with diabetes in relation to the selected period of time led to an undesirable blood glucose level during at least part of the selected period of time, then the second-type insulin dosage suggestion can be modified accordingly.

Figure 6A:
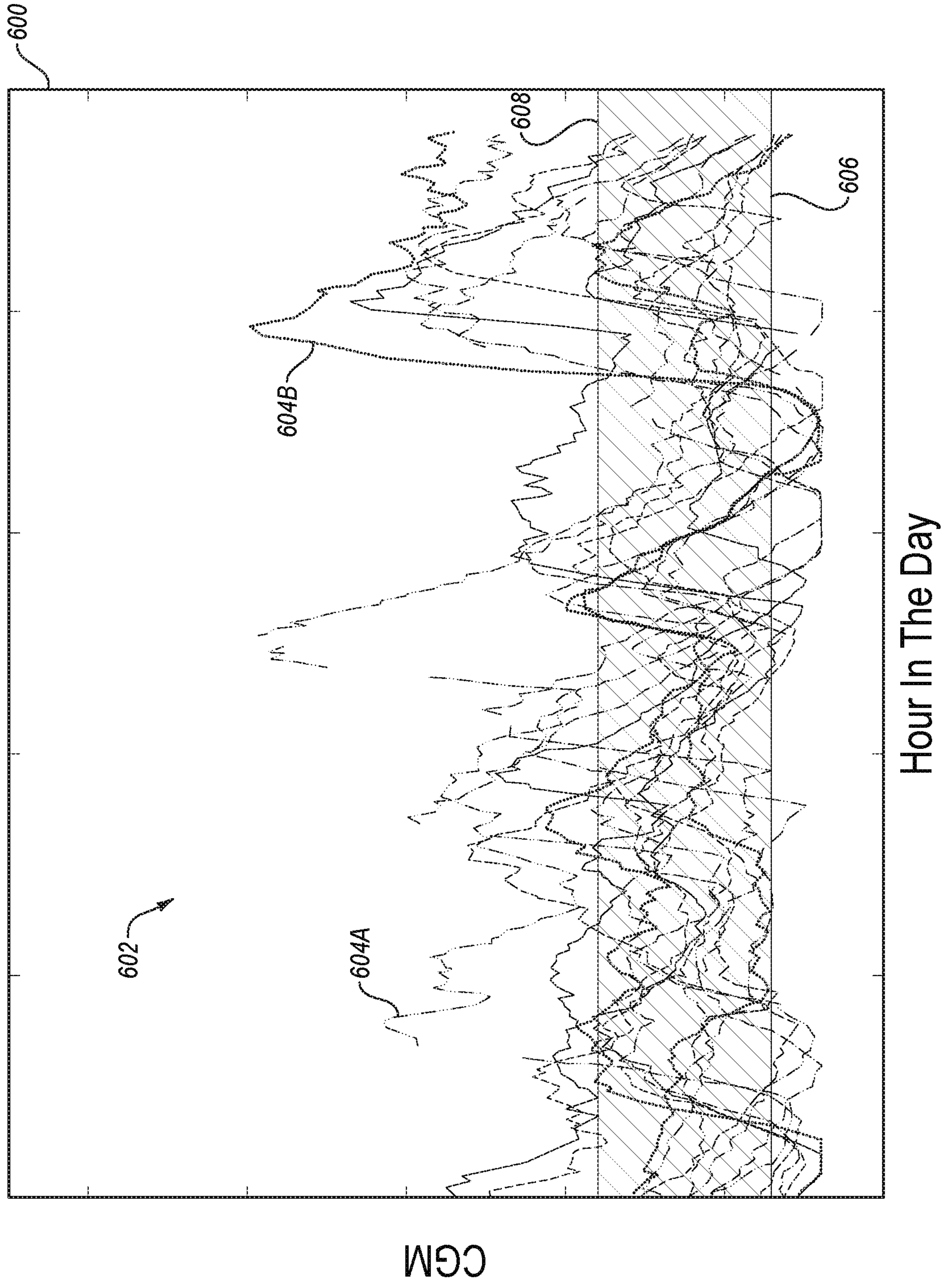
FIGS. 6A-C show examples of analysis of blood glucose data.
Figure 6B:
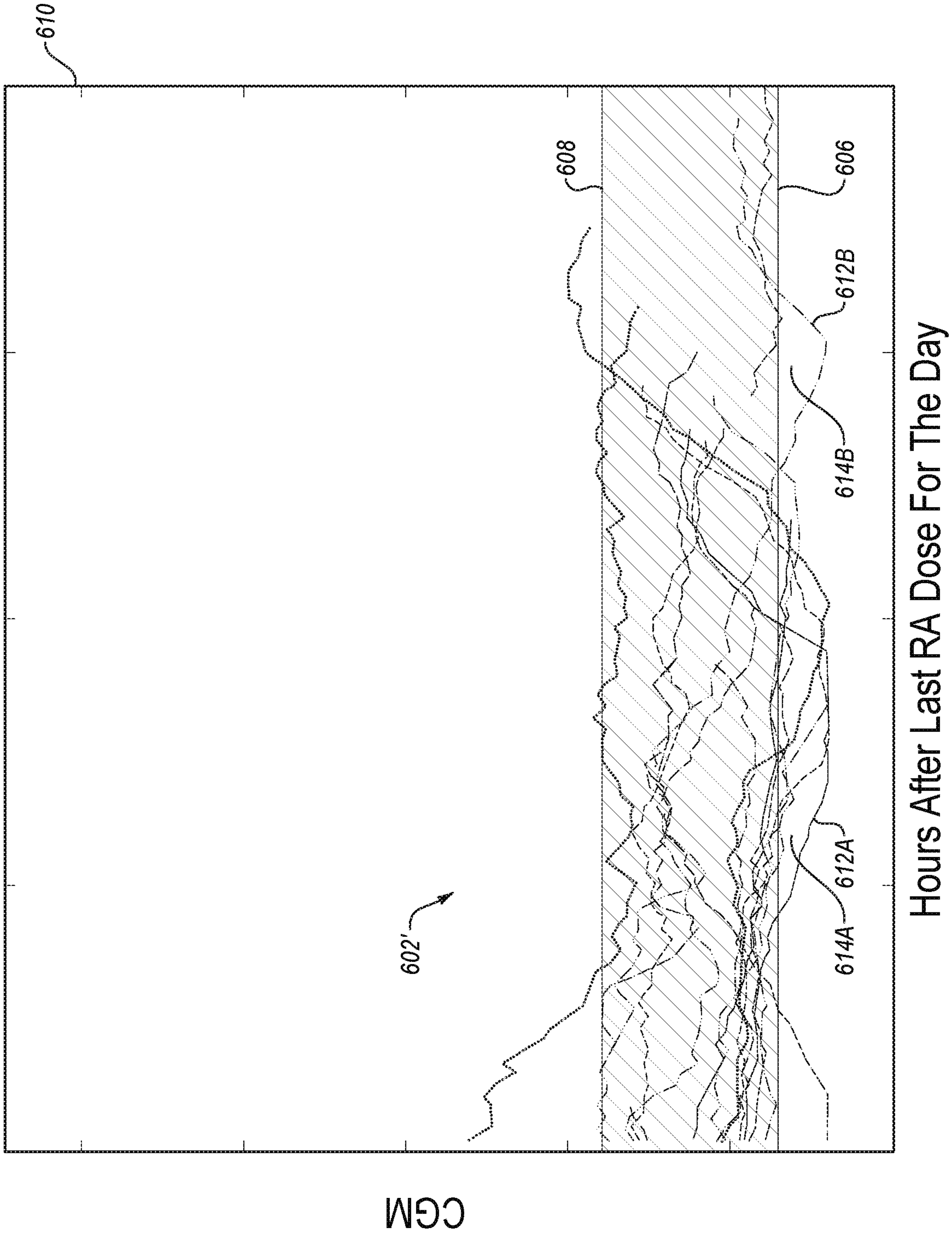
Figure 6C:
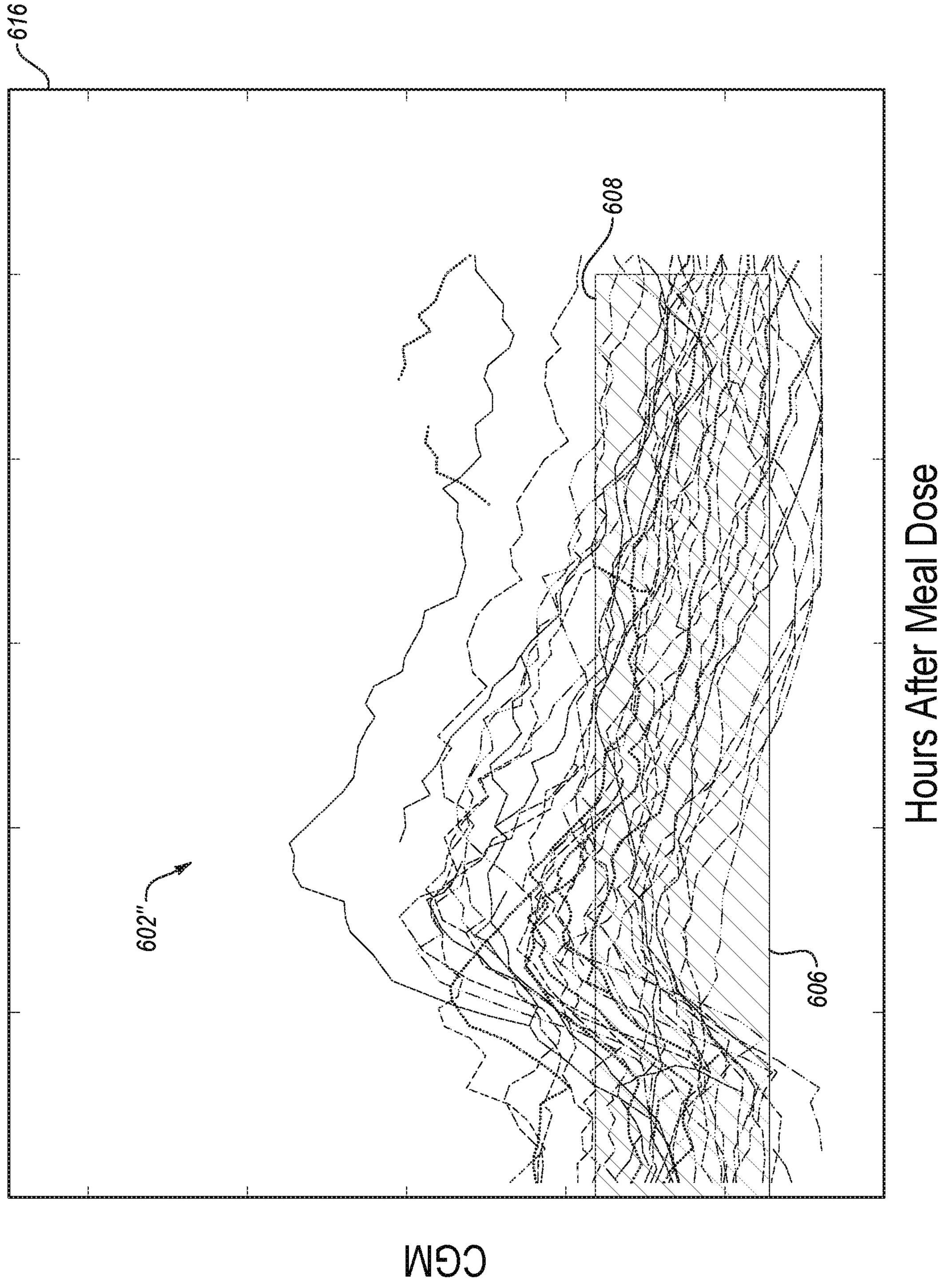

FIGS. 6A-C show examples of analysis of blood glucose data. The analysis illustrated in these examples can be used in combination with, or can include aspects of, one or more other examples described elsewhere herein.

FIG. 6A shows a graph 600 that contains blood glucose data 602. The values of the blood glucose data 602 (e.g., the reading of a CGM or another glucose monitor or another glucose sensor), are measured against the vertical axis of the graph 600. For example, values of the blood glucose data 602 can be measured in milligrams per deciliter (mg/dL). The temporal distribution of the values of the blood glucose data 602 is indicated against the horizontal axis. For example, values of the blood glucose data 602 can be measured in a number of hours after a selected starting point.

The blood glucose data 602 is for a specific person with diabetes and can represent a plurality of days. In some implementations, more than one week's worth of data can be used. For example, the blood glucose data 602 is here collected during a time period of about fourteen days. The blood glucose data 602 is here presented in multiple time segments from the plurality of days that correspond to each other. For example, a graph 604A corresponds to one 24-hour period during the fourteen days (optionally with one or more gaps in the data), and a graph 604B corresponds to another 24-hour period (optionally with one or more gaps in the data). That is, each of the graphs 604A-B, which are only two of the multiple graphs formed by the blood glucose data 602, indicates the estimated blood glucose values of the person with diabetes during a particular 24-hour period.

One or more thresholds for the blood glucose data 602 can be defined in the graph 600. In some implementations, a low threshold for blood glucose can be defined. For example, a threshold 606 here corresponds to a blood glucose value of about 70 mg/dL. In some implementations, a high threshold for blood glucose can be defined. For example, a threshold 608 here corresponds to a blood glucose value of about 180 mg/dL. That is, the graph 600 here indicates how the blood glucose data 602 has varied relative to the thresholds 606 and 608 over the course of the plurality of days. In some implementations, a variable such as time-in-range can be defined relating to the amount of time where the blood glucose value was between the thresholds 606 and 608. For example, time-in-range can refer to the percentage of time spent between the thresholds 606 and 608.

Particular portions of the blood glucose data 602 can be separated out from other portions for further analysis. In some implementations, data corresponding to sleeping time or other fasting time is of interest. FIG. 6B shows an example of a graph 610 that contains blood glucose data 602', wherein the blood glucose data 602' is a subset of the blood glucose data 602 in FIG. 6A. The axes of the graph 610 may be the same as, or equivalent to, those of the graph 600. The thresholds 606 and 608 for the blood glucose data 602' are indicated in the graph 610.

The blood glucose data 602' is here presented in multiple time segments from the plurality of days that correspond to each other. For example, a graph 612A corresponds to one fasting time period during the fourteen days, and a graph 612B corresponds to another fasting time period. That is, each of the graphs 612A-B, which are only two of the multiple graphs formed by the blood glucose data 602', indicates the estimated blood glucose values of the person with diabetes during a particular fasting time period. The blood glucose data 602' may have been selected so that the graphs 612A-B, and each of the other graphs formed by the blood glucose data 602', begins a certain time period after an identified event. In some implementations, that event is a most recent ingestion of rapid-acting insulin. For example, the time axis of the graph 610 may begin a specific number of hours (including, but not limited to, six hours) after the rapid-acting insulin ingestion. Moreover, each of the graphs 612A-B and the other graphs formed by the blood glucose data 602' may continue until the person with diabetes ingests another dose of rapid-acting insulin, or ingests another meal, whichever comes first. The rapid-acting insulin dosage time can be determined in any suitable way, including, but not limited to, by detecting one or more capping events relating to a pen cap for an insulin injection pen.

The graph 610, or the blood glucose data 602', can be used for observing or evaluating the impact of a dose of insulin having an active time longer than the active time of rapid-acting insulin. For example, the impact of long-acting insulin can be observed or evaluated. One or more metrics can be applied to at least some of the blood glucose data 602' as part of evaluation. At least one of such metrics can be designed to determine a variability of the blood glucose data 602'.

A cost function can be applied as a metric to evaluate one or more types of insulin (e.g., long-acting and/or rapid-acting insulin). A cost function can also or instead be referred to as a loss function. The cost function can evaluate differences between blood glucose values and blood glucose targets. For example, the blood glucose targets can be specified for a diurnal time segment. The insulin therapy can then be selected or adjusted to produce the lowest cost function value. Any suitable cost function can be used. In some implementations, a cost function can sum the absolute value of the difference between each blood glucose value and each blood glucose target. In some implementations, a cost functions can use square of the difference. In some implementations, a cost function can use a logarithmic function of the difference between each blood glucose value and each blood glucose target. In some implementations, a cost function can use the square of a logarithmic function of the difference between each blood glucose value and each blood glucose target. In some implementations, a cost function can assign a higher cost to blood glucose values below a blood glucose target in order reduce the risk of a hypoglycemic event. In some implementations, a cost function can include a summation of absolute values of a plurality of predicted deviations, squared deviations, log squared deviations, or a combination thereof. In some implementations, a cost function can include variables unrelated to the predicted blood glucose values. For example, a cost function can include a penalty for profiles that do not deliver 100% of a baseline basal rate of insulin dosage. In some implementations, a cost function can provide a slight preference to keep an existing basal modification.

An area-under-the-curve (AUC) evaluation can be performed as a metric to evaluate one or more types of insulin. The AUC evaluation can generate one or more AUC values for the blood glucose data, the AUC value representing a quality aspect of the insulin therapy. In the graph 610, one or more AUC evaluations can be performed with regard to the blood glucose data 602'. For example, an area 614A can be determined that corresponds to the area under the curve for the graph 612A with regard to the threshold 606 (more specifically, the area between the graph 612A and the threshold 606). As another example, an area 614B can be determined that corresponds to the area under the curve for the graph 612B with regard to the threshold 606 (more specifically, the area between the graph 612B and the threshold 606).

A counting of data points can be performed as a metric to evaluate one or more types of insulin. In some implementations, each of the graphs 612A-B and the other graphs formed by the blood glucose data 602' is formed by a series of data points. Each data point is associated with a blood glucose value and the time when the blood glucose value was registered (e.g., by a CGM). The system can determine how many data points of the blood glucose data 602', or of an individual graph such as the graph 612A or 612B, fall below the threshold 606. If the metric indicates at least a certain number of points, the insulin therapy (e.g., rapid-acting and/or long-acting insulin dosages) can be modified accordingly. Alternatively or additionally, a determination of time below the threshold can be performed as a metric to evaluate one or more types of insulin.

Referring again briefly to FIG. 6A, other particular portions of the blood glucose data 602 can be separated out from yet other portions for further analysis. In some implementations, data corresponding to glucose after meals is of interest. FIG. 6C shows an example of a graph 616 that contains blood glucose data 602", wherein the blood glucose data 602" is another subset of the blood glucose data 602 in FIG. 6A than the blood glucose data 602' in FIG. 6B. The axes of the graph 616 may be the same as, or equivalent to, those of the graph 600. The thresholds 606 and 608 for the blood glucose data 602' are indicated in the graph 610.

One or more metrics can be applied to at least some of the blood glucose data 602" as part of evaluation. For example, any of the metrics described with reference to FIG. 6B, or describe elsewhere herein, can be applied to the blood glucose data 602". At least one of such metrics can be designed to determine a variability of the blood glucose data 602".

Figure 7:
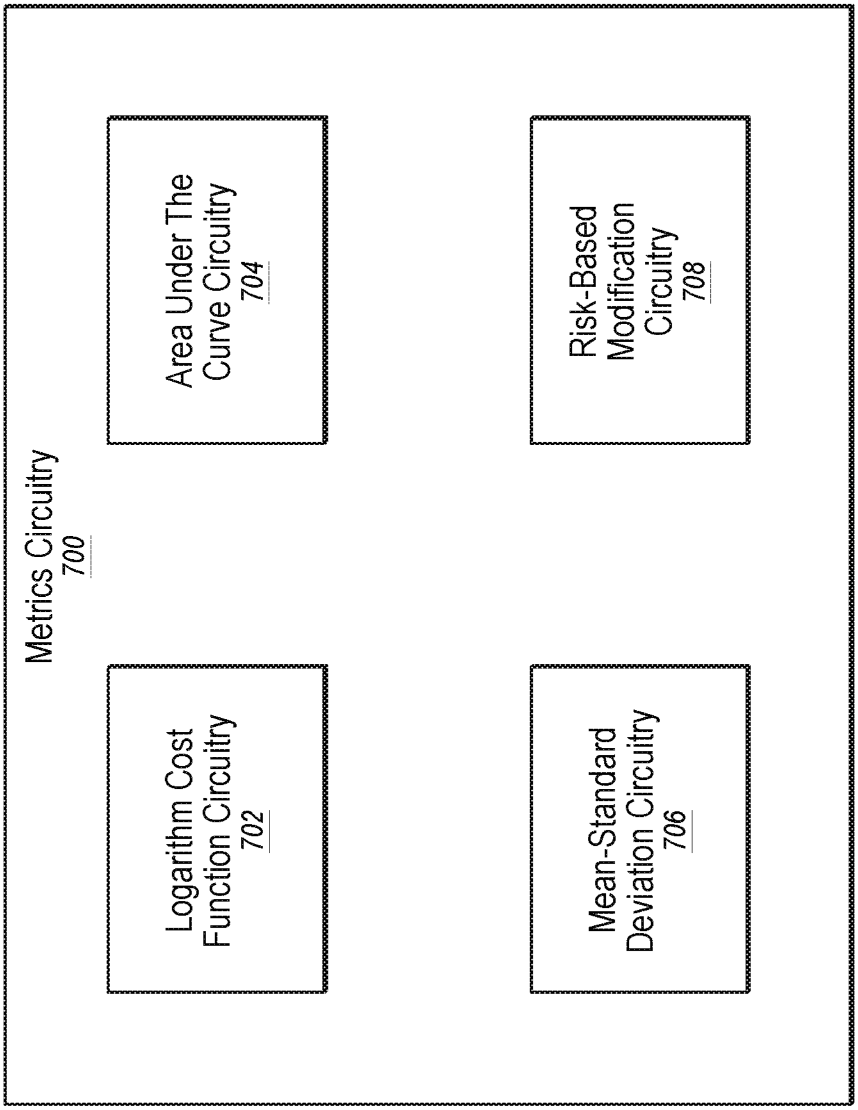
FIG. 7 shows a diagram of an example of metrics circuitry.

FIG. 7 shows a diagram of an example of metrics circuitry 700. The metrics circuitry 700 can be used in combination with, or can include aspects of, one or more other examples described elsewhere herein. The metrics circuitry 700 can include one or more electronic components arranged as circuitry, for example as described below with reference to FIG. 14.

The metrics circuitry 700 can determine a variability of some or all values with blood glucose data. In some implementations, any measure of dispersion can be determined as part of evaluating the variability of the blood glucose values. Dispersion can be represented by measures including, but not limited to, a geometric mean of the blood glucose values, a geometric standard deviation of the blood glucose values, a midspread of the blood glucose values, a range of the blood glucose values, a mean absolute difference of the blood glucose values, a median absolute deviation of the blood glucose values, an average absolute deviation of the blood glucose values, and a distance standard deviation of the blood glucose values. In some implementations, the difference between the blood glucose values and a blood glucose threshold can be taken into account. As such, determining a variability for blood glucose values for a selected period of time can include determining a measure of dispersion for the blood glucose values for the selected period of time.

In some implementations, a percentage of the blood glucose values that are below (or above) a threshold (e.g., the threshold 606 and/or 608 in FIGS. 6A-C) can be determined. For example, it can be determined what percentage of the blood glucose values of the blood glucose data 602 in FIG. 6A (or the blood glucose data 602' or 602") exceed the threshold. As such, determining a measure of dispersion can include determining a percentage of blood glucose values for a selected period of time that fall below a threshold blood glucose level.

The insulin therapy can be modified in response to a determination of a percentage of the blood glucose values that are below (or above) a threshold. In some implementations, if the percentage exceeds a threshold percentage, the insulin dosage suggestion for that type of insulin (e.g., long-acting or rapid-acting insulin) can be decreased (or increased). For example, if the determination of the measure of dispersion (e.g., the variability) indicates that more than, say, about 4% of the values of the blood glucose data 602 in FIG. 6A (or the blood glucose data 602' or 602") are above the threshold 608 (which can be considered as exceeding the threshold, in one example), then the insulin dosage suggestion can be increased for at least one type of insulin. As another example, if the determination of the measure of dispersion (e.g., the variability) indicates that at most about 4%, or less than about 4%, of the values of the blood glucose data 602 in FIG. 6A (or the blood glucose data 602' or 602") are below the threshold 606 (which can be considered as exceeding the threshold, in one example), then the insulin dosage suggestion can be decreased for at least one type of insulin.

The metrics circuitry 700 can include a logarithm cost function circuitry 702. The logarithm cost function circuitry 702 can evaluate one or more logarithm-based cost functions for blood glucose values. In some implementations, the logarithm cost function circuitry 702 can take into account one or more target blood glucose values and evaluate data for a selected period of time. For example, the logarithm cost function circuitry 702 can evaluate the square of the logarithm of the difference (e.g., the "loss") between the blood glucose value of the person with diabetes and the target blood glucose value(s). In some implementations, the logarithm cost function circuitry 702 evaluates fasting data (e.g., the blood glucose data 602' in FIG. 6B). In some implementations, the logarithm cost function circuitry 702 evaluates post-meal data (e.g., the blood glucose data 602" in FIG. 6B).

The metrics circuitry 700 can include an AUC circuitry 704. The AUC circuitry 704 can evaluate one or more areas where the blood glucose values of a graph transgress a blood glucose threshold limit or threshold value. In some implementations, the AUC circuitry 704 can take into account one or more blood glucose thresholds and evaluate data for a selected period of time. For example, the AUC circuitry 704 can evaluate the area of the graph where the blood glucose values for the person with diabetes are below (or above) a corresponding threshold. In some implementations, the AUC circuitry 704 evaluates fasting data (e.g., the blood glucose data 602' in FIG. 6B). In some implementations, the AUC circuitry 704 evaluates post-meal data (e.g., the blood glucose data 602" in FIG. 6B). In some implementations, the AUC circuitry 704 can determine an AUC value (e.g., the measure of the area) for a selected period of time.

The metrics circuitry 700 can include a mean-standard deviation circuitry 706. The mean-standard deviation circuitry 706 relates to a distribution of blood glucose values, where a mean and a standard deviation may be, or have been, determined. For example, the mean and/or standard deviation can be take into account in one or more metrics used for evaluating an insulin therapy setting. Examples are described with reference to FIG. 8.

The metrics circuitry 700 can include a risk-based modification circuitry 708. The risk-based modification circuitry 708 performs modification of one or more insulin therapies. In some implementations, the risk-based modification circuitry 708 can adjust one or more settings for an insulin therapy. For example, the risk-based modification circuitry 708 can increase or decrease the setting regarding at least one type of insulin.

Figure 8:
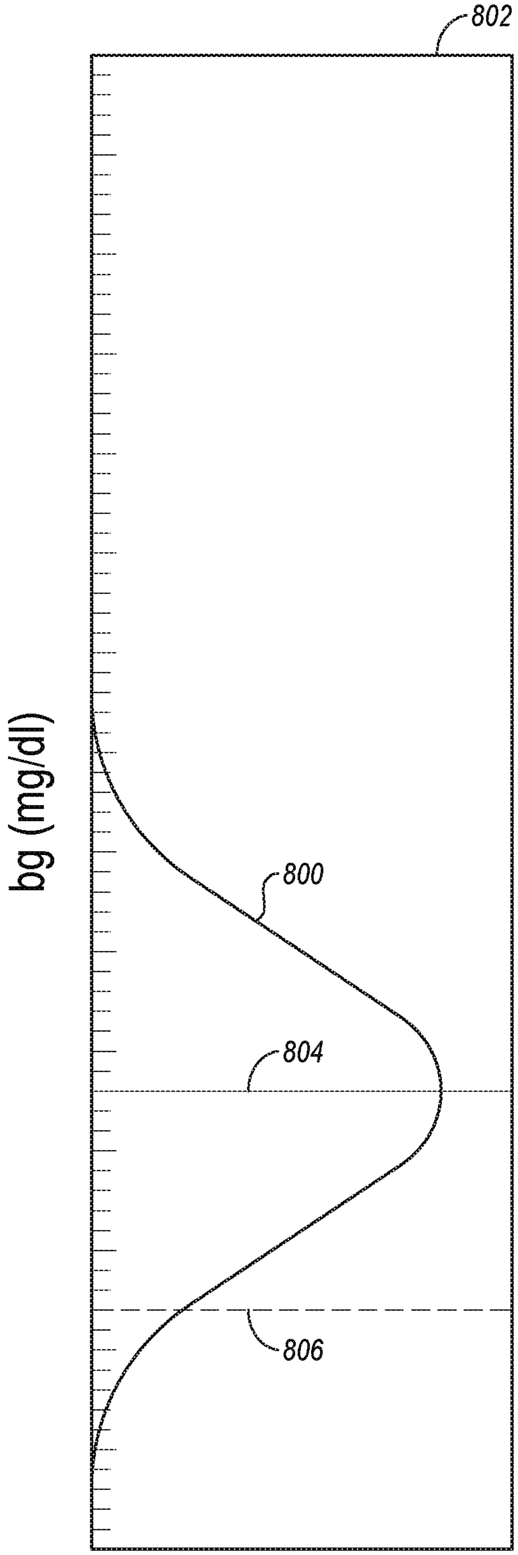
FIG. 8 shows an example of a distribution of blood glucose values.

FIG. 8 shows an example of a distribution of blood glucose values. The distribution 800 is shown in a diagram 802 where the vertical axis indicates blood glucose level (e.g., in the unit of mg/dL), and the horizontal axis indicates the number (or percentage) of data points having a certain blood glucose value.

The distribution 800 is here log normal, and is presented and evaluated using a logarithmic scale. The distribution 800 has most common value 804 (e.g., ninety-four mg/dL). For the distribution 800, with a threshold level 806 (e.g., 70 mg/dL), approximately five percent of the distribution 800 is below the threshold level 806. For the distribution 800, for five percent of the distribution to be below the threshold level 806, the most common value 804 may be observed. Stated another way, if the distribution 800 were observed and five percent was the desired percentage below the threshold level 806 of seventy mg/dL (e.g., the mean minus a multiple of the standard deviation was desired to be seventy mg/dL), methods and systems of the present disclosure may operate to shift the distribution 800 towards the most common value 804. The distribution 800 may be more or less spread out than another distribution, and thus, the distribution 800 may have a higher corresponding mean blood glucose level (i.e., the most common value 804) corresponding to the same percentage of the distribution falling below the threshold level 806.

The mean-standard deviation circuitry 706 can evaluate the distribution 800. In some implementations, the mean-standard deviation circuitry 706 can take into account one or more blood glucose thresholds and evaluate data for a selected period of time. For example, the mean-standard deviation circuitry 706 can determine a geometric mean (e.g., equal to most common value 804) of the distribution 800 (sometimes referred to as mu*). For example, the mean-standard deviation circuitry 706 can determine a standard deviation of the distribution 800. In some implementations, a difference depending on the mean and the standard deviation can be evaluated. A multiple of the standard deviation can be subtracted from the mean. For example, with the distribution 800, a blood glucose value corresponding to the mean less three standard deviations can be evaluated as a metric regarding whether to modify any insulin dosage suggestion. That is, determining a measure of dispersion can include evaluating a mean value of a distribution of the blood glucose values for a selected period of time, and a standard deviation of the distribution of the blood glucose values for the selected period of time.

A risk-based dispersion determination can be performed. In some implementations, the mean-standard deviation circuitry 706 can perform a risk-based dispersion determination to determine a variability of blood glucose values. A goal of the risk-based dispersion determination can be to keep the blood glucose values of the person with diabetes within a particular range, or above and/or below a certain blood glucose threshold. In some implementations, a goal may be that the person with diabetes should only have less than a particular likelihood (e.g., about 4%) of having blood glucose values that are below about 70 mg/dL. For this and/or other purposes, a predefined mean value (sometimes referred to as mu*_preferred) can be defined. In some implementations, the predefined mean value can correspond to the following relationship:

$$mu^*_{preferred} = 70 \times (\text{sigma}^*)^{1.7507},$$

where sigma* is the geometric standard deviation, and $$mu^*_{preferred}$$

is the preferred geometric mean.

One or more conditions can be evaluated. In some implementations, a buffer value (sometimes referred to as "buffer") is considered. For example, the buffer can be defined as $$\text{buffer} = \text{effect of } \max(1 \text{ unit}, 10\% \text{ dose change}) = ISF \times \max(1 \text{ unit}, 10\% \text{ dose change}),$$

where ISF is an insulin sensitivity factor for the person with diabetes. In some implementations, ISF expresses the expected reduction of the glucose in the blood for each unit of insulin delivered. For example, ISF (sometimes referred to as correction factor) can be expressed as mg/dL/unit or mmol/L/unit.

For example, if the following relationship is true $$mu^* - \text{buffer} \leq mu^*_{preferred},$$

then a decision can be made to decrease the dose.

As another example, if the following relationship is true $$mu^* + \text{buffer} \geq mu^*_{preferred},$$

then a decision can be made to increase the dose.

Regarding a carbohydrate-to-insulin ratio (sometimes referred to as CR), the mean and standard deviation can be calculated or otherwise determined regarding about 4-6 hours after the most recent dose of rapid-acting insulin. In some implementations, CR can be used to express the relationship between grams of carbohydrate and units of insulin for an individual. For example, CR can indicate the number of grams of carbohydrates that one unit of insulin will offset.

Regarding the ISF, the mean and standard deviation can be calculated or otherwise determined regarding about 4-6 hours after the most recent dose of rapid-acting insulin with a correction bolus.

Regarding long-acting insulin dosage, the mean and standard deviation can be calculated or otherwise determined beginning about 6 hours after the most recent dose of rapid-acting insulin, if enough data is available. Otherwise, the main and standard deviation can be calculated or otherwise determined beginning about 4 hours after the most recent dose of rapid-acting insulin.

Alternatives to the above approaches can exist. In some implementations, the change regarding long-acting insulin can be done based on mu*+buffer alone. In some implementations, for increasing the dose, the mean-standard deviation circuitry 706 can look for an increasing pattern in addition to a relatively high mu*.

As such, determining a variability of blood glucose values can include evaluating a relationship between a mean value of a distribution of the blood glucose values for a selected period of time, and a predefined mean value. For example, evaluating the relationship can include comparing the predefined mean value to the mean value with a buffer value added to the mean value, and comparing the predefined mean value to the mean value with the buffer value subtracted from the mean value.

Figure 9:
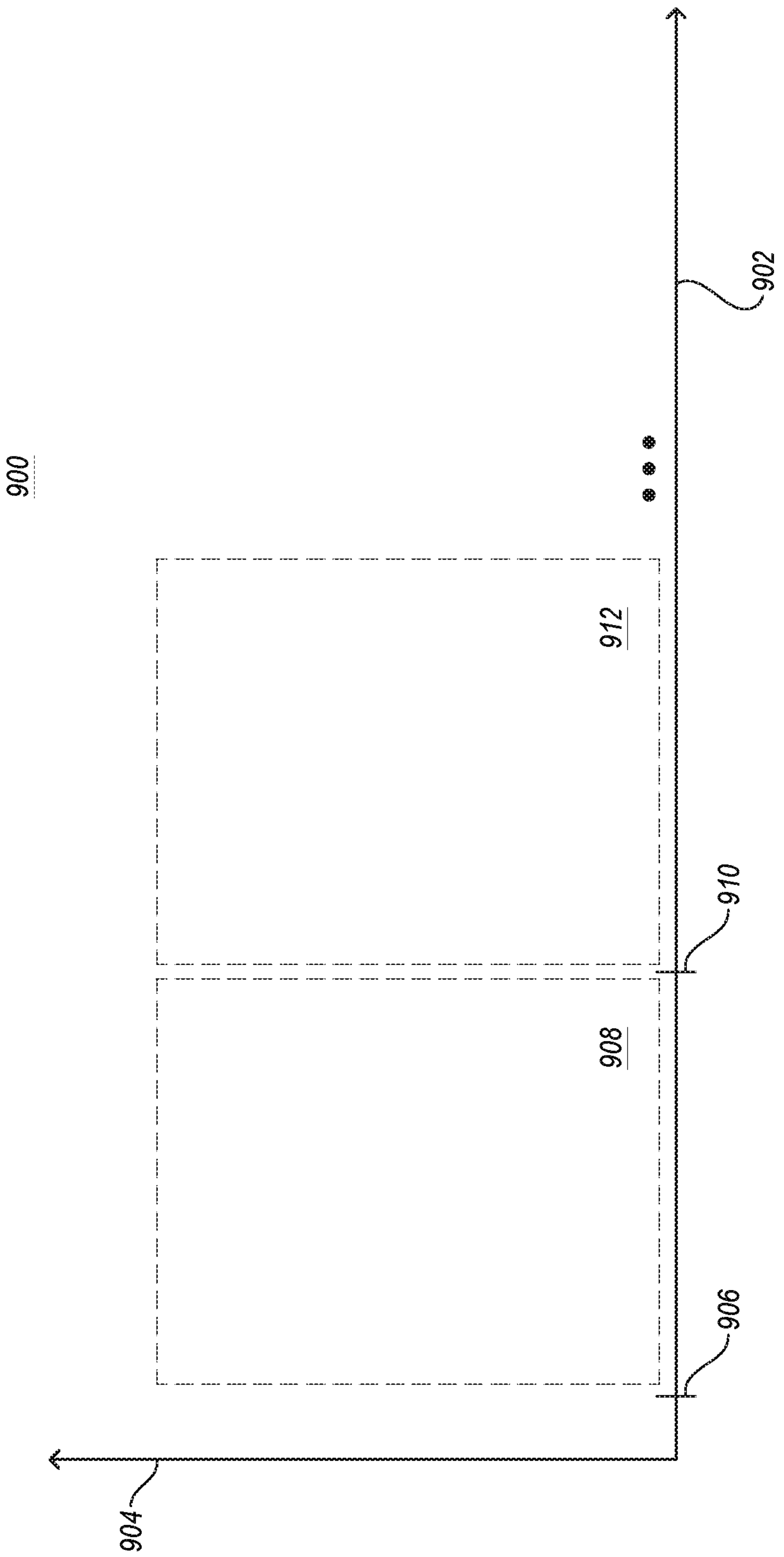
FIG. 9 shows an example of selecting time periods for evaluating blood glucose data.

FIG. 9 shows an example of selecting time periods for evaluating blood glucose data. The following examples can be used in combination with, or can include aspects of, one or more other examples described elsewhere herein.

A diagram 900 includes a horizontal axis 902 relative to which time can be indicated, and a vertical axis 904 relative to which a measure of insulin therapy successfulness can be indicated. In some implementations, the vertical axis 904 indicates a measured or estimated level of blood glucose in a person with diabetes (e.g., measured in mg/dL).

A dosage time 906 is here indicated on the horizontal axis 902. In some implementations, the dosage time 906 corresponds to the actual, estimated, or inferred point in time when the person with diabetes ingested insulin. For example, the dosage time 906 can correspond to a most recent ingestion of rapid-acting insulin (e.g., as indicated by one or more capping events of a pen cap, as determined by monitoring a cap sensor on the pen cap).

A data inclusion area 908 is schematically indicated in the diagram 900. In some implementations, the data inclusion area 908 is positioned to begin at, in conjunction with, or based on, the dosage time 906, and to extend for a predefined amount of time thereafter. For example, the data inclusion area 908 can correspond to a certain number of hours immediately following ingestion of a dose of rapid-acting insulin. The data inclusion area 908 indicates at least one type of data from a greater data trove, such as a collection of blood glucose data over a plurality of days, that may be identified for analysis. For example, when evaluating the success of a rapid-acting insulin therapy, data falling within the data inclusion area 908 can be separated from the rest of the data and subjected to analysis (e.g., the blood glucose data 602" in FIG. 6C may be identified from among the blood glucose data 602 in FIG. 6A, based on the data inclusion area 908). For example, variability of blood glucose values can be determined for a selected period of time, and the data inclusion area 908 can define how the period of time is selected.

A time 910 is indicated on the horizontal axis 902. In some implementations, the time 910 corresponds to the actual, estimated, or inferred point in time when the person with diabetes is considered to begin fasting. For example, the time 910 can correspond to a time following sufficiently long after a most recent ingestion of rapid-acting insulin that it can be assumed only long-acting insulin will be affecting the person with diabetes (until a next dose of rapid-acting insulin).

A data inclusion area 912 is schematically indicated in the diagram 900. In some implementations, the data inclusion area 912 is positioned to begin at, in conjunction with, or based on, the time 910, and to extend for a predefined amount of time thereafter. For example, the data inclusion area 912 can correspond to a certain number of hours immediately following the time when the most recently ingested dose of rapid-acting insulin is deemed to no longer be active or active to any significant extent (e.g., this can be considered fasting time or sleeping time). That is, the data inclusion area 912 can be considered as following the data inclusion area 908. In other words, the period of time of the data inclusion area 912 can be following the period of time of the data inclusion area 908. Analysis can be performed on the data corresponding to the data inclusion area 912 whether or not any data corresponding to the data inclusion area 908 (or any other data inclusion area) is also being analyzed.

The data inclusion area 912 indicates at least one type of data from a greater data trove, such as a collection of blood glucose data over a plurality of days, that may be identified for analysis. In some implementations, when evaluating the success of a long-acting insulin therapy, data falling within the data inclusion area 912 can be separated from the rest of the data and subjected to analysis (e.g., the blood glucose data 602' in FIG. 6B may be identified from among the blood glucose data 602 in FIG. 6A, based on the data inclusion area 912). For example, variability of blood glucose values can be determined for a selected period of time, and the data inclusion area 912 can define how the period of time is selected. More or fewer data inclusion areas than the data inclusion areas 908 and 912 can be used. In some implementations, the data inclusion area 912 is defined based on the length of time between the dosage time 906 and the time 910, although the data inclusion area 908—that is, the extent during which data relating to the dosage ingested at the dosage time 906 may be shorter than such a length of time. That is, a type of insulin (e.g., rapid-acting) can be analyzed during a first period of time (e.g., corresponding to the data inclusion area 908), and another type of insulin (e.g., long-acting) can be analyzed during a second period of time (e.g., corresponding to the data inclusion area 912). In such a scenario, the second period of time can be selected as beginning after a third period of time (e.g., the length of time between the dosage time 906 and the time 910) following a dosage time of the first-mentioned type of insulin.

Figure 10:
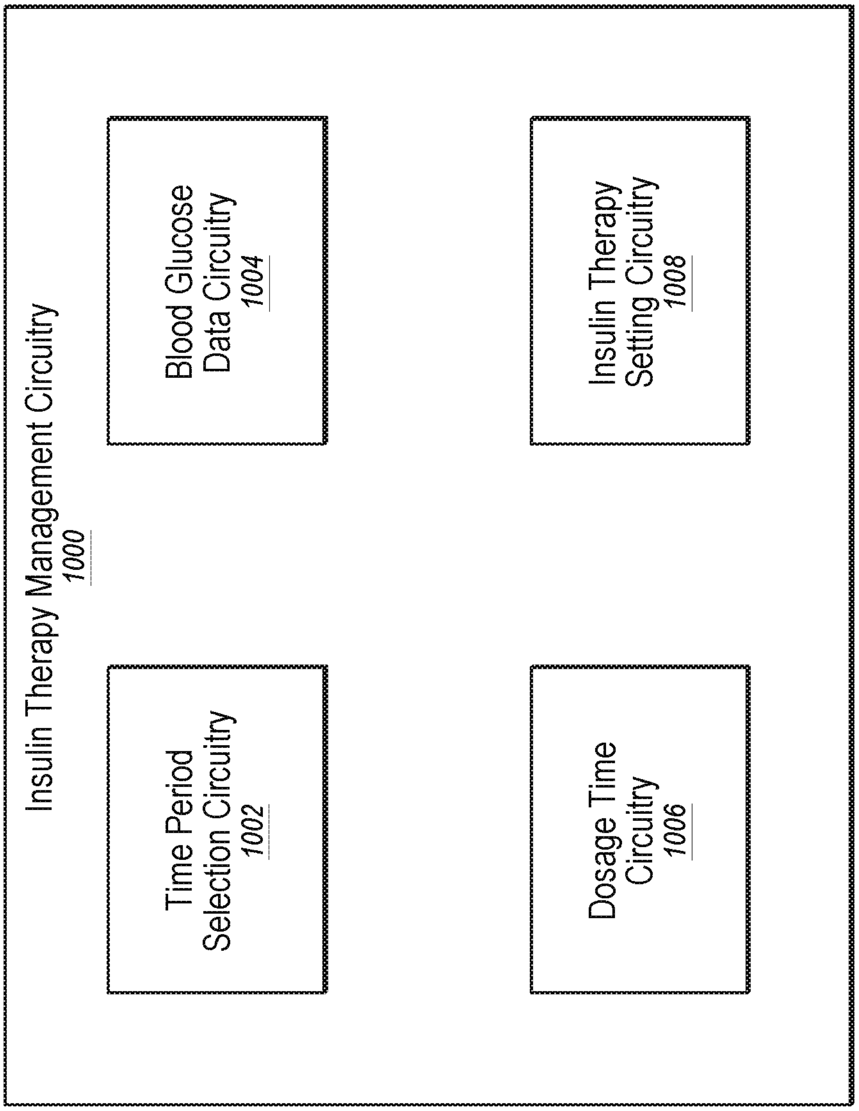
FIG. 10 shows a diagram of an example insulin therapy management circuitry.

FIG. 10 shows a diagram of an example insulin therapy management circuitry 1000. The insulin therapy management circuitry 1000 can be used in combination with, or can include aspects of, one or more other examples described elsewhere herein. The insulin therapy management circuitry 1000 can include one or more electronic components arranged as circuitry, for example as described below with reference to FIG. 14.

The insulin therapy management circuitry 1000 includes time period selection circuitry 1002. In some implementations, the time period selection circuitry 1002 can identify one or more times (e.g., the dosage time 906 and/or the time 910 in FIG. 9), and use it/them to select a time period (e.g., by defining the data inclusion area 908 and/or the data inclusion area 912 in FIG. 9). The time period selection circuitry 1002 can make use of other information in making the selection of the time period(s). In some implementations, the time period selection circuitry 1002 can refer to a known active time for a particular type of insulin, and/or diurnal patterns for the person with diabetes, to name just two examples.

The insulin therapy management circuitry 1000 includes blood glucose data circuitry 1004. In some implementations, the blood glucose data circuitry 1004 can select one or more subsets of blood glucose data relating to a person with diabetes. The selection can be made for the purpose of performing analysis, such as a determination of variability, on the data. For example, the blood glucose data circuitry 1004 can select the blood glucose data 602' in FIG. 6B and/or the blood glucose data 602" in FIG. 6C. The blood glucose data circuitry 1004 can refer to one or more periods of time selected by the time period selection circuitry 1002 in identifying the data.

The insulin therapy management circuitry 1000 includes dosage time circuitry 1006. The dosage time circuitry 1006 can identify dosage times for a person with diabetes. A dosage time can be an actual dosage time, an estimated dosage time, or an inferred dosage time, to name just some examples. In some implementations, the dosage time circuitry 1006 monitors a cap sensor of a pen cap for an insulin injection pen. For example, the dosage time circuitry 1006 can make use of the micro switch 324, optical sensor(s) 326, and/or position sensor(s) 328 in FIG. 3 to determine whether the person with diabetes has taken insulin. Data from the dosage time circuitry 1006 can be provided to at least one other component within or outside the insulin therapy management circuitry 1000, including, but not limited to, the blood glucose data circuitry 1004.

The insulin therapy management circuitry 1000 includes insulin therapy setting circuitry 1008. The insulin therapy setting circuitry 1008 can manage insulin therapy for one or more persons with diabetes. For each person with diabetes, the insulin therapy setting circuitry 1008 can control one or more settings. A setting can relate to the dose of a type of insulin. In some implementations, the insulin therapy setting circuitry 1008 can manage insulin dosage suggestions for a first type of insulin (e.g., rapid-acting insulin) and a second type of insulin (e.g., long-acting insulin) for the person with diabetes. For example, the insulin therapy setting circuitry 1008 can modify the insulin dosage suggestion (e.g., by increasing or decreasing the suggested dosage) based on analysis.

The insulin therapy management circuitry 1000 is an example of a diabetes management device (e.g., implemented in the pen cap 110 and/or 112, or the remote user interface device 108, or the glucose monitor 106 or another glucose sensor, of FIG. 1). The diabetes management device can include a processor (e.g., the processor 314 in FIG. 3 and/or processing device 1402 in FIG. 14), and a non-transitory storage medium (e.g., the data storage (or memory) 316 in FIG. 3 and/or secondary storage device 1414 and/or system memory 1404 in FIG. 14). The non-transitory storage medium has stored therein a first-type insulin dosage suggestion for a person with diabetes regarding a first type of insulin (e.g., the insulin dosage suggestion 206 in FIG. 2). The first type of insulin has an active time that is longer than an active time for a second type of insulin. The non-transitory storage medium has stored therein blood glucose data for the person with diabetes (e.g., the blood glucose data 602 in FIG. 6A), the blood glucose data including blood glucose values for a plurality of days. The non-transitory storage medium has stored therein instructions (e.g., the time period selection circuitry 1002, blood glucose data circuitry 1004, dosage time circuitry 1006, and/or insulin therapy setting circuitry 1008 in FIG. 10) that when executed cause the processor to perform operations. The operation can include determining a first variability (e.g., using one or more metrics on the blood glucose data 602' in FIG. 6B) of the blood glucose values for a selected first period of time (e.g., as shown in the graph 610 in FIG. 6B) during the plurality of days. The operation can include modifying the first-type insulin dosage suggestion (e.g., increasing or decreasing the suggested dose) in the non-transitory storage medium based on the determined first variability. One or more modified insulin dosage suggestion can be output (e.g., visually or audibly presented) to the person with diabetes.

Figure 11:
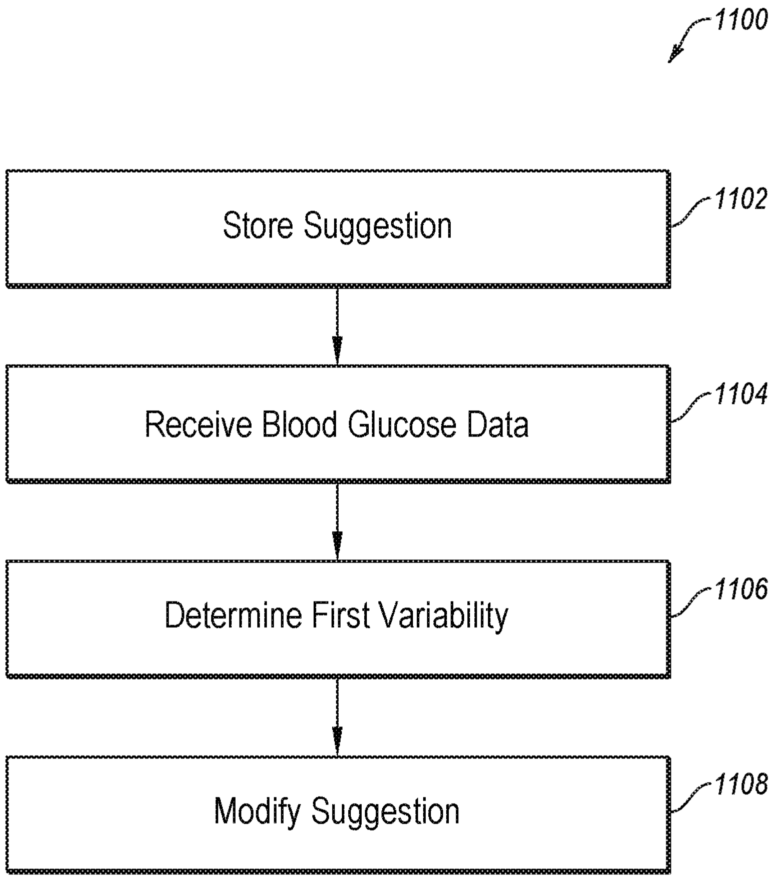
FIGS. 11 and 12 show examples of methods.
Figure 12:
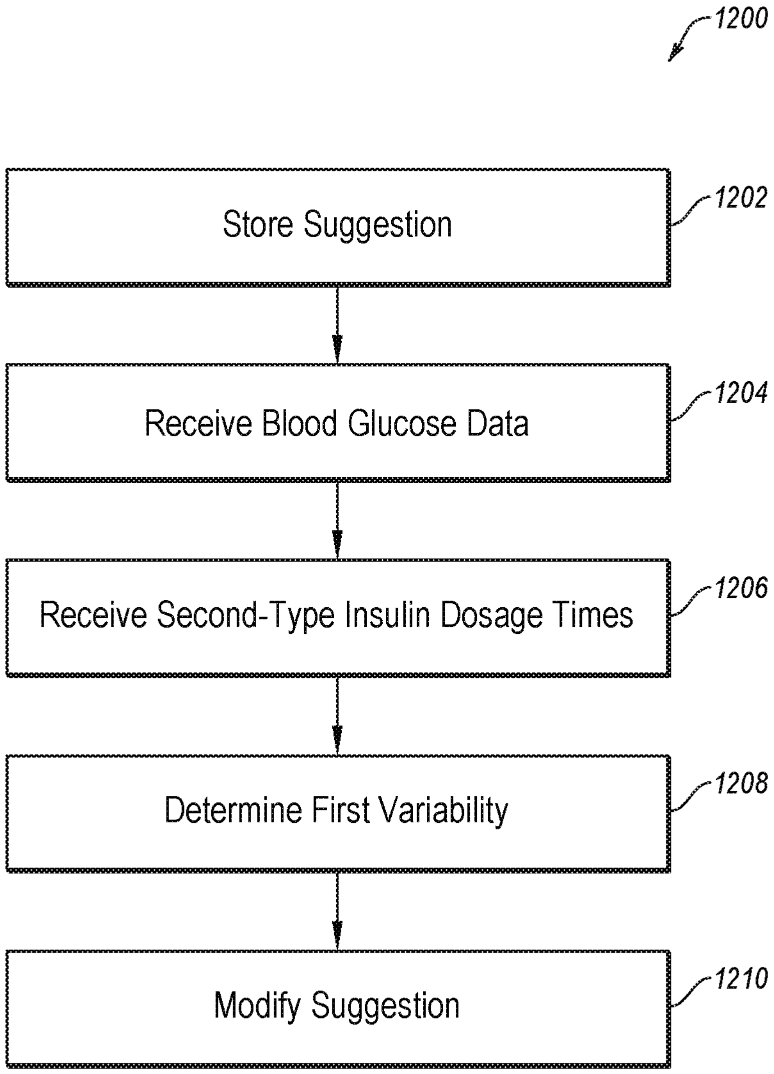

FIGS. 11 and 12 show examples of methods. FIG. 11 shows a method 1100 and FIG. 12 shows a method 1200. The method 1100 and/or 1200 can be used in combination with, or can include aspects of, one or more other examples described elsewhere herein. More or fewer operations can be performed in the method 1100 and/or 1200. Two or more operations in the method 1100 and/or 1200 can be performed in a different order, unless otherwise indicated.

At 1102, the method 1100 includes storing, in a non-transitory storage medium of an electronic device, a first-type insulin dosage suggestion for a person with diabetes regarding a first type of insulin having an active time that is longer than an active time for a second type of insulin. For example, the insulin dosage suggestion 206 in FIG. 2A can be stored in pen cap 110 and/or 112, or the remote user interface device 108, or the glucose monitor 106 or another glucose sensor, of FIG. 1.

At 1104, the method 1100 includes receiving blood glucose data for the person with diabetes, the blood glucose data including blood glucose values for a plurality of days. For example, the blood glucose data circuitry 1004 can receive the blood glucose data 602 in FIG. 6A.

At 1106, the method 1100 includes determining a first variability of the blood glucose values for a selected first period of time during the plurality of days. For example, the blood glucose data circuitry 1004 can determine variability using one or more metrics, including, but not limited to, as exemplified herein.

At 1108, the method 1100 includes modifying the first-type insulin dosage suggestion in the non-transitory storage medium based on the determined first variability. For example, the insulin therapy setting circuitry 1008 can modify the insulin dosage suggestion 206 in FIG. 2A.

That is, the method 1100 is an example of modifying a first-type insulin dosage suggestion. In the same or other implementations, a second-type insulin dosage suggestion can instead or additionally be modified.

Regarding the method 1200, at 1202 it includes storing, in a non-transitory storage medium of an electronic device, a second-type insulin dosage suggestion for a person with diabetes regarding a second type of insulin having an active time that is shorter than an active time for a first type of insulin. For example, one or more of the insulin dosage suggestions in FIG. 2B can be stored in pen cap 110 and/or 112, or the remote user interface device 108, or the glucose monitor 106 or another glucose sensor, of FIG. 1.

At 1204, the method 1200 includes receiving blood glucose data for the person with diabetes, the blood glucose data including blood glucose values for a plurality of days. For example, the blood glucose data circuitry 1004 can receive the blood glucose data 602 in FIG. 6A.

At 1206, the method 1200 includes receiving second-type insulin dosage times for the person with diabetes regarding the plurality of days. For example, the dosage time circuitry 1006 can detect, determine, estimate, or infer one or more dosage times for a person with diabetes.

At 1208, the method 1200 includes determining a first variability of the blood glucose values for a selected first period of time during the plurality of days. For example, the blood glucose data circuitry 1004 can determine variability using one or more metrics, including, but not limited to, as exemplified herein.

At 1210, the method 1200 includes modifying the second-type insulin dosage suggestion in the non-transitory storage medium based on the determined first variability. For example, the insulin therapy setting circuitry 1008 can modify one or more of the insulin dosage suggestions in FIG. 2B.

Figure 13A:
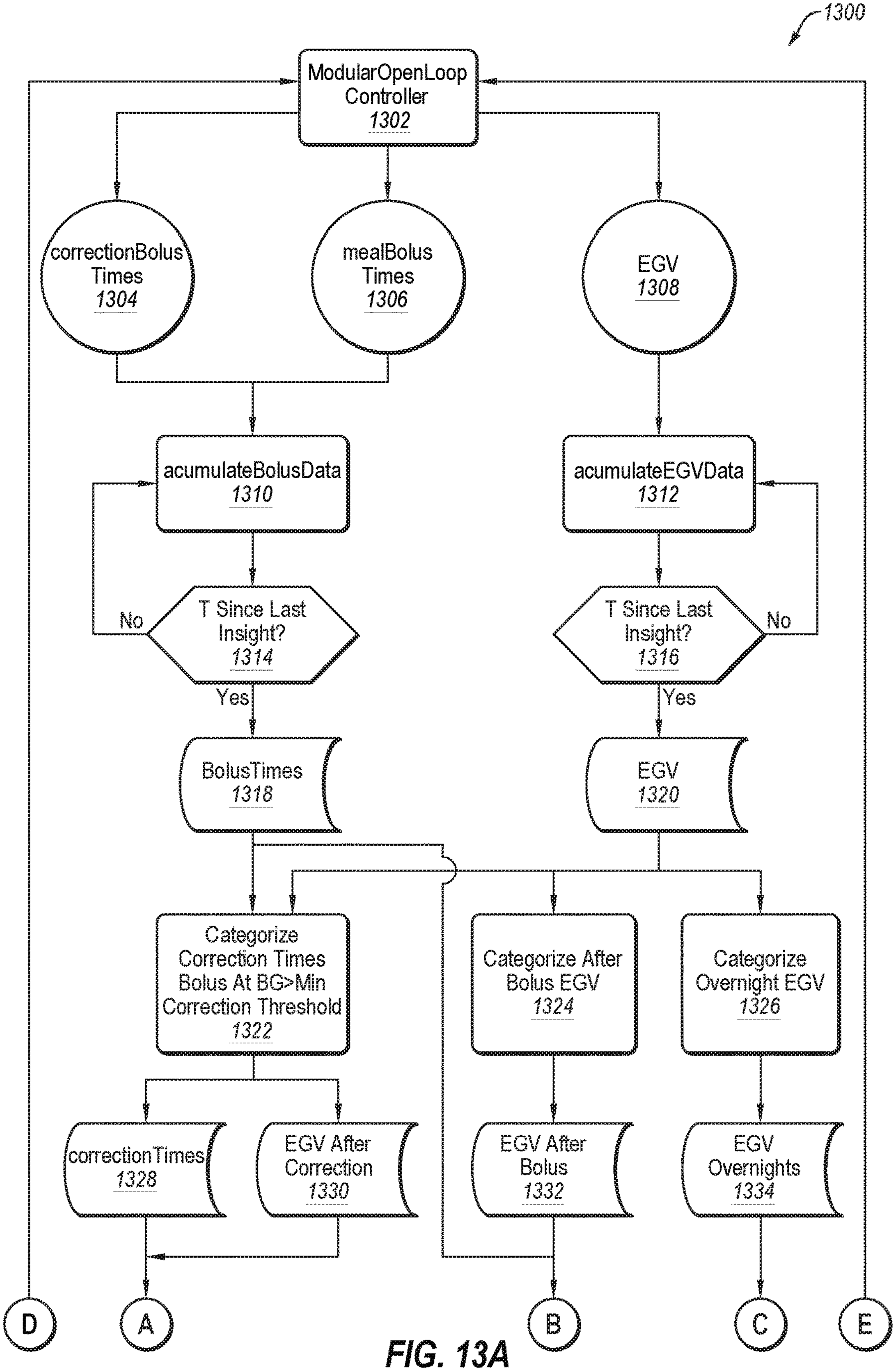
FIGS. 13A-C show an example of a process.
Figure 13B:
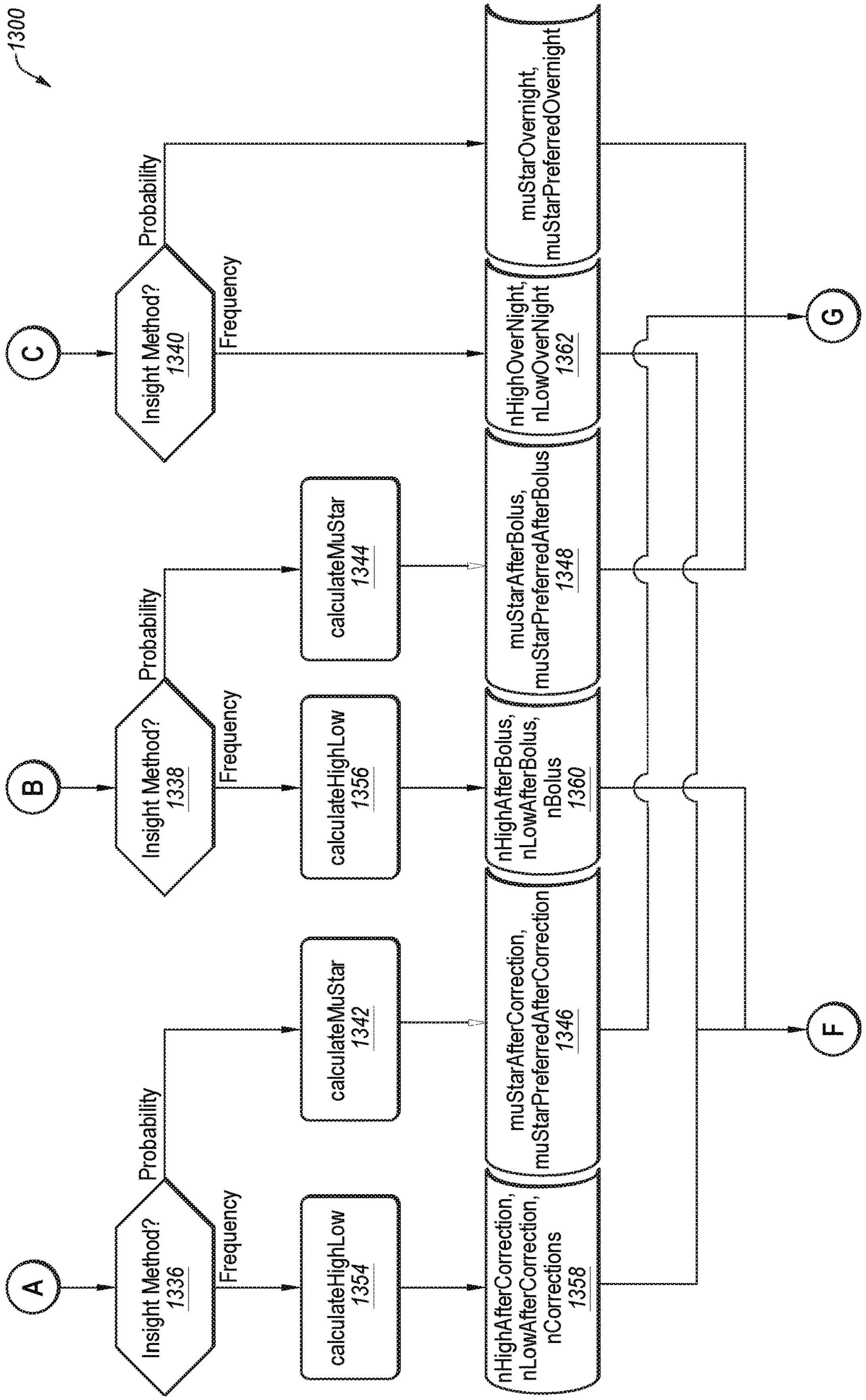
Figure 13C:
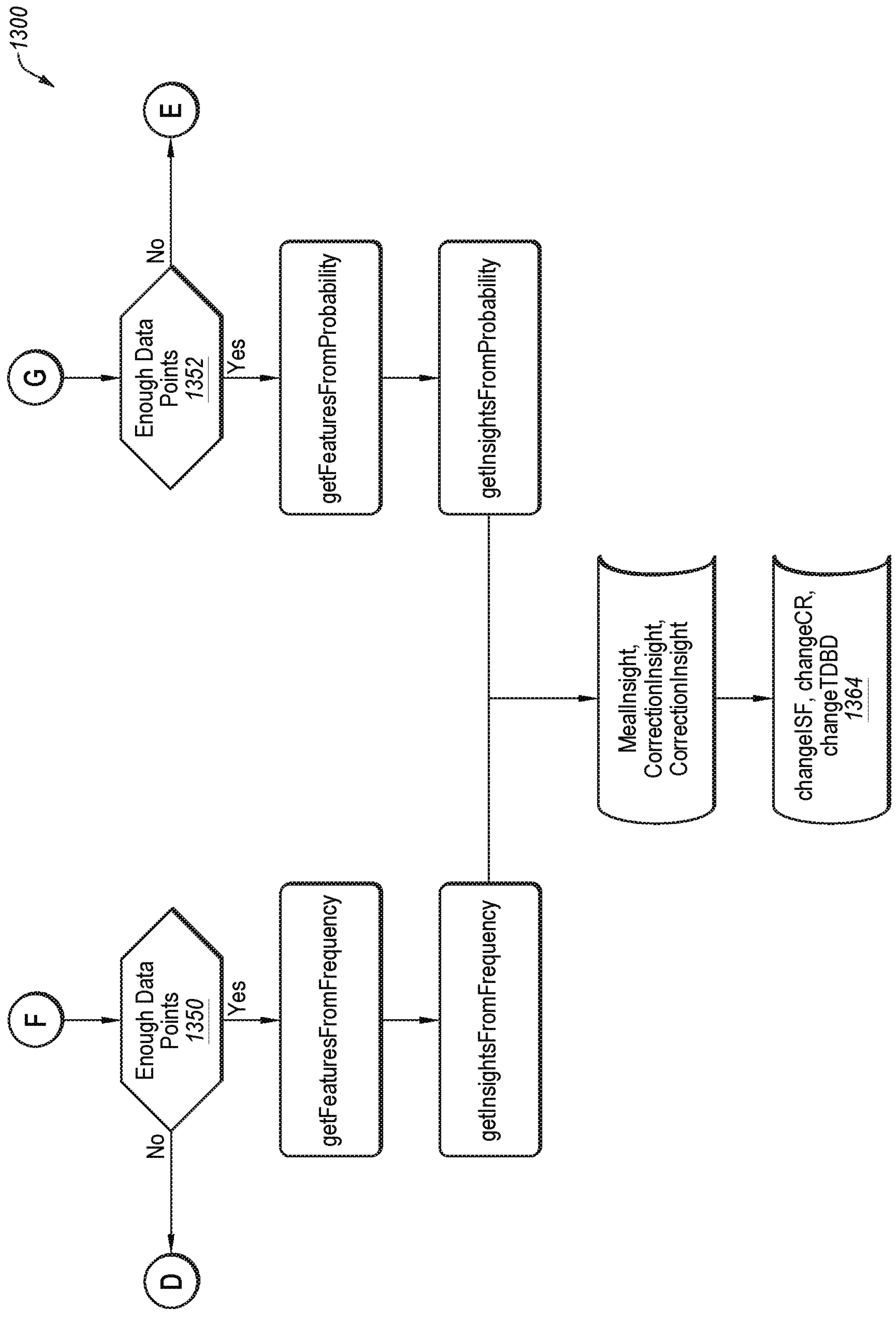

FIGS. 13A-C show an example of a process 1300. The process 1300 can be used in combination with, or can include aspects of, one or more other examples described elsewhere herein. More or fewer operations can be performed in the process 1300. Two or more operations in the process 1300 can be performed in a different order, unless otherwise indicated.

In some implementations, the process 1300 is performed in connection with an open loop controller 1302 (e.g., implemented in the glucose monitor 106, pen cap 110 and/or 112, or the remote user interface device 108 in FIG. 1). For example, the open loop controller 1302 can be a modular open loop controller that enables various optional features by instantiating objects implementing one or more specific features. The process 1300 illustrates how data can be accumulated from the open loop controller 1302 and when processing can be performed on the data. In some implementations, the open loop controller 1302 can provide correction bolus times 1304, meal bolus times 1306, and an estimated glucose value (EGV) 1308. The correction bolus times 1304, meal bolus times 1306, and/or the EGV 1308 can be provided at a sampling rate.

The correction bolus times 1304, meal bolus times 1306, and/or the EGV 1308 can be accumulated in a buffer until a period of time T is reached. Here, the correction bolus times 1304 and the meal bolus times 1306 are accumulated in a buffer 1310. Here, the EGV 1308 is accumulated in a buffer 1312. The process 1300 can include a decision 1314 to determine, for the correction and meal data, whether a predefined time T has elapsed since the last "insight" by the diabetes management system. In some implementations, an insight is a suggestion generated by the diabetes management system. For example, the insight can suggest a behavior and/or a dosing update based on data. If the time T has not elapsed, the process 1300 can return to the buffer 1310. The process 1300 can include a decision 1316 to determine, for the EGV data, whether a predefined time T has elapsed since the last "insight" by the diabetes management system. If the time T has not elapsed, the process 1300 can return to the buffer 1312.

When the time T has elapsed for the correction and meal data, the process 1300 can begin processing the data of time length T. In some implementations, the correction and meal bolus data can be combined into a single stream of data. To process the buffered data, a subset of the bolus data can be extracted from the buffer based on the EGV reading at the same time. Here, the process 1300 includes bolus data 1318 and EGV data 1320. If the EGV reading at the time of a bolus is exceeded, this bolus time is saved in a separate buffer and categorized as a correction bolus. The original bolus times can remain in the original buffer unaltered. For example, they can be assumed to be all meal bolus times. For each bolus time saved, a preconfigured offset from that bolus time and duration of EGV reading are saved in a structure or array, for example. This can be done for the buffers containing correction bolus and meal bolus times. Here, the process 1300 includes a categorization 1322 relating to "categorize correction times bolus at BG>min correction threshold," a categorization 1324 relating to "categorize after bolus EGV," and a categorization 1326 relating to "categorize overnight EGV" In some implementations, along with EGV readings associated with bolus times, a section of time that is identified as overnight can be used as the boundaries to save the overnight EGV readings. Processing can be performed for each section of EGV data associated with meal, correction bolus and overnight. In some implementations, the period T can be multiple days. For example, there can then be multiple overnight sections that the process 1300 can process along with additional meal and correction bolus sections. Here, the process 1300 includes data 1328 relating to correction times, data 1330 relating to EGV after correction, data 1332 relating to EGV after bolus, and data 1334 relating to EGV overnights.

With data properly categorized and sections of EGV data extracted and associated with each category, the process 1300 can select a method or approach to make decisions. For example, such decision(s) can include whether to increase or decrease rapid acting and/or long acting insulin. Depending on the specified option to identify patterns of highs or lows, a threshold-based or probability-based method or approach can be used. Here, the process 1300 includes decisions 1336, 1338, and 1340, each relating to whether the decision(s) should be based on frequency or probability.

When the probability-based approach is used, an actual geometric mean, a standard deviation, and a preferred geometric mean can be calculated for each section of time associated with a bolus or overnight time span. The process 1300 can include operations 1342 and 1344, each relating to calculating mu*. In some implementations, this is done for all sections of time for each category. For example, a geometric mean and a standard deviation can be calculated for all EGV data associated with corrections together. In some implementations, these values are calculated for all meal bolus EGV data together and all overnight EGV data together. Depending on the value of the actual geometric mean compared to the preferred, a pattern can be identified whether the subject is too high or too low. The process 1300 can include data 1346 relating to mu* after correction and a preferred mu* after correction, and data 1348 relating to mu* after bolus and a preferred mu* after bolus.

Before the process 1300 proceeds, a check can be performed to ensure that enough high and low events have occurred for each type of threshold type. For example, this can provide reliable information when calculating the thresholds. Here, the process 1300 includes decisions 1350 and 1352, each relating to whether there are enough data points. If not enough events have occurred to make a decision, the process 1300 may recommend no changes in the insulin therapy.

With the actual and preferred mu* calculated, a pattern should be identified for each category. For example, this can include correction, meal and overnight. A logic can be applied to relevant data. The logic can take into account whether the actual mu* is greater or smaller than the preferred mu*. For example, if the actual mu* for time spans after correction is less than the preferred mu* after correction, the pattern identified for correction rapid-acting insulin can be that less is required. This can be performed for all categories, resulting in patterns for rapid-acting insulin for meals, rapid-acting insulin for correction, and long-acting insulin.

A preferred geometric mean for post-meal and correction bolus can be given as:

$$\mu^*_{preferred} = \max\left(120, \mu^*_{prob\,low<x,2-6\,hr\ post\,RA)}, \mu^*_{(prob\,low<y,4-6\,hr\ \ post\,RA)}\right),$$

where RA stands for rapid-acting insulin.

The preferred geometric mean for the overnight time span can be given as:

$$\mu^*_{preferred} = \max\left(120, \mu^*_{(prob,low<z)}\right).$$

In the above formulas, x, y, and z are variables that can be further optimized.

With a complete set of features calculated for each category, a final recommendation can be made. For example, this can involve how rapid-acting insulin for meal and corrections, and/or long-acting insulin, need to be adjusted. Additional logic can be used to ensure safety and stability of the process 1300. In some implementations, long-acting insulin changes can be prioritized over rapid-acting insulin changes. For example, rapid-acting insulin changes can have a long-term effect. If all three categories are showing a decrease required in rapid-acting insulin for meal and correction and in long-acting insulin, a decrease can be recommended. Various combinations of the features can be considered for different possible scenarios.

When the frequency method or approach is used, the process 1300 can first count the number of highs or lows for each post bolus section of time and overnight section of time individually. For example, if observing after a specific meal bolus time plan, the EGV goes below a lower threshold for a predetermined amount of time, the counts as a single instance of a low. Depending on the individual event along with other conditions, an event can be identified as requiring more, less, or no change in insulin for the specific category. This can be done throughout the time spanning that section of data and all the individual instances are identified. Other instances in the same categories can be identified for other sections of data. Here, process 1300 includes operations 1354 and 1356, each relating to calculation of high and/or low. The process 1300 includes data 1358 relating to high after correction, low after correction, and corrections; data 1360 relating to high after bolus, low after bolus, and bolus; and data 1362 relating to high overnight, and low overnight.

The number of events can be checked to ensure that enough information is provided to allow the rest of the process 1300 to make a decision. If not enough data points are available for any of the categories, the process 1300 can return a recommendation to make no changes and continue collecting data.

Events identified as being high, low, or in range, that require more, less, or no change in insulin, respectively, can be identified for correction, meals, and overnight categories. These can be counted to obtain a total. A total can be divided by the total number of corrections, meals or overnights to get a frequency of increase or decrease insulin required. The operations of calculating frequencies in the process 1300 are referred to as "getFeaturesFrom."

In some implementations, the mapping to get the frequencies from frequencies of lows/highs can be:

- Correction highs: need increase in rapid-acting insulin for corrections
- Correction lows: need decrease in rapid-acting insulin for corrections
- Meal highs: need increase in rapid-acting insulin for meals
- Meal lows: need decrease in rapid-acting insulin for meals
- Overnight highs: need increase in long-acting insulin
- Overnight lows: need decrease in long-acting insulin With the frequencies of increase or decrease now available for each category, they can be compared to preconfigured thresholds for each category. If for any of the frequencies calculated, the respective threshold is exceeded, for that specific category, there may have been a pattern identified as requiring more or less insulin. A case could occur that both exceed the threshold requiring both more and less insulin. For example, if the frequency of lows after corrections which is the frequency of requiring more rapid-acting insulin for corrections exceeds its respective threshold, the pattern of requiring more rapid-acting insulin for corrections can be applied.

These may be the individual patterns identified of requiring increase, decrease or no change for each category. In some implementations, they are not used alone to make decisions. For example, combinations of all the identified patterns can be important to make decisions. With the frequency of each pattern identified, logic can be applied in the same manner as patterns identified using the probability method. For example, if overnight frequency of lows exceeds the threshold, then a decrease in long-acting insulin can be recommended. For example, this can be the case with required decrease in long-acting insulin and frequency of meal lows. For example, this can be the case with required decrease in meal rapid-acting insulin and no highs or lows for correction rapid-acting insulin. The long-acting, rapid-acting meal, and rapid-acting correction insights can be generated. The operations of generating insights in the process 1300 are referred to as "getInsightsFrom," which results in the long-acting, rapid-acting meal, and rapid-acting correction insights.

Once the results are generated for all meal, correction and overnight time spans, a set of insights can be available that will be used to determine if long-acting or rapid-acting doses need to be adjusted. The rapid-acting increase or decrease insight can be unique for the after-meal bolus and the correction bolus in addition to the overnight insight which recommends adjustment for the long-acting insulin.

To ensure that insights are applied in a stable and safe manner another set of decisions can be made based on insights recommending increase or decrease of long-acting or rapid-acting insulin. These decisions can be outlined in a table where a +1 entry indicates an increase in the dose quantity, a −1 entry indicates a decrease, and a 0 entry indicates no change in insulin dose. For rapid-acting insulin the increase or decrease can be separately applied to the meal bolus and the correction bolus.

At operation 1364, an increase or decrease to the three individualization parameters, CR, ISF and total daily basal dose (TDBD) can be performed. These parameters can be used as proxies to increase and decrease the effective rapid-acting insulin for meal and correction bolus and the long-acting insulin dose. This can effectuate changes to effective rapid-acting and long-acting insulin.

Figure 14:
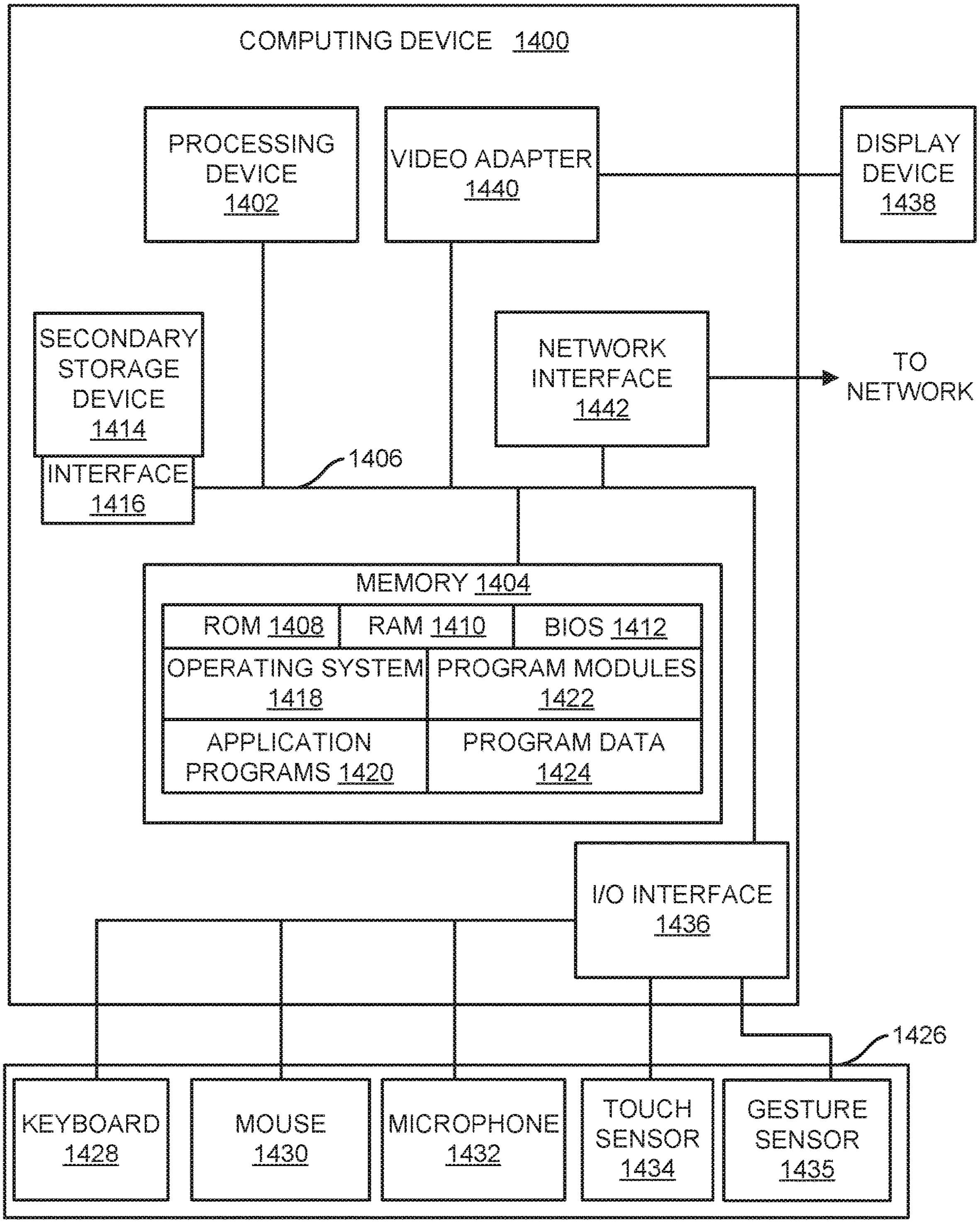
FIG. 14 shows an example of a computer device that can be used to implement the techniques described here.

FIG. 14 illustrates an example architecture of a computing device 1400 that can be used to implement aspects of the present disclosure, including any of the systems, apparatuses, and/or techniques described herein, or any other systems, apparatuses, and/or techniques that may be utilized in the various possible embodiments.

The computing device illustrated in FIG. 14 can be used to execute the operating system, application programs, and/or software modules (including the software engines) described herein.

The computing device 1400 includes, in some embodiments, at least one processing device 1402 (e.g., a processor), such as a central processing unit (CPU). A variety of processing devices are available from a variety of manufacturers, for example, Intel or Advanced Micro Devices. In this example, the computing device 1400 also includes a system memory 1404, and a system bus 1406 that couples various system components including the system memory 1404 to the processing device 1402. The system bus 1406 is one of any number of types of bus structures that can be used, including, but not limited to, a memory bus, or memory controller; a peripheral bus; and a local bus using any of a variety of bus architectures.

Examples of computing devices that can be implemented using the computing device 1400 include a desktop computer, a laptop computer, a tablet computer, a mobile computing device (such as a smart phone, a touchpad mobile digital device, or other mobile devices), or other devices configured to process digital instructions.

The system memory 1404 includes read only memory 1408 and random access memory 1410. A basic input/output system 1412 containing the basic routines that act to transfer information within computing device 1400, such as during start up, can be stored in the read only memory 1408.

The computing device 1400 also includes a secondary storage device 1414 in some embodiments, such as a hard disk drive, for storing digital data. The secondary storage device 1414 is connected to the system bus 1406 by a secondary storage interface 1416. The secondary storage device 1414 and its associated computer readable media provide nonvolatile and non-transitory storage of computer readable instructions (including application programs and program modules), data structures, and other data for the computing device 1400.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media. Additionally, such computer readable storage media can include local storage or cloud-based storage.

A number of program modules can be stored in secondary storage device 1414 and/or system memory 1404, including an operating system 1418, one or more application programs 1420, other program modules 1422 (such as the software engines described herein), and program data 1424. The computing device 1400 can utilize any suitable operating system, such as Microsoft Windows™, Google Chrome™ OS, Apple OS, Unix, or Linux and variants and any other operating system suitable for a computing device. Other examples can include Microsoft, Google, or Apple operating systems, or any other suitable operating system used in tablet computing devices.

In some embodiments, a user provides inputs to the computing device 1400 through one or more input devices 1426. Examples of input devices 1426 include a keyboard 1428, mouse 1430, microphone 1432 (e.g., for voice and/or other audio input), touch sensor 1434 (such as a touchpad or touch sensitive display), and gesture sensor 1435 (e.g., for gestural input. In some implementations, the input device(s) 1426 provide detection based on presence, proximity, and/or motion. In some implementations, a user may walk into their home, and this may trigger an input into a processing device. For example, the input device(s) 1426 may then facilitate an automated experience for the user. Other embodiments include other input devices 1426. The input devices can be connected to the processing device 1402 through an input/output interface 1436 that is coupled to the system bus 1406. These input devices 1426 can be connected by any number of input/output interfaces, such as a parallel port, serial port, game port, or a universal serial bus. Wireless communication between input devices 1426 and the input/output interface 1436 is possible as well, and includes infrared, BLUETOOTH® wireless technology, 802.11a/b/g/n, cellular, ultra-wideband (UWB), ZigBee, or other radio frequency communication systems in some possible embodiments, to name just a few examples.

In this example embodiment, a display device 1438, such as a monitor, liquid crystal display device, projector, or touch sensitive display device, is also connected to the system bus 1406 via an interface, such as a video adapter 1440. In addition to the display device 1438, the computing device 1400 can include various other peripheral devices (not shown), such as speakers or a printer.

The computing device 1400 can be connected to one or more networks through a network interface 1442. The network interface 1442 can provide for wired and/or wireless communication. In some implementations, the network interface 1442 can include one or more antennas for transmitting and/or receiving wireless signals. When used in a local area networking environment or a wide area networking environment (such as the Internet), the network interface 1442 can include an Ethernet interface. Other possible embodiments use other communication devices. For example, some embodiments of the computing device 1400 include a modem for communicating across the network.

The computing device 1400 can include at least some form of computer readable media. Computer readable media includes any available media that can be accessed by the computing device 1400. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 1400.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 14 is also an example of programmable electronics, which may include one or more such computing devices, and when multiple computing devices are included, such computing devices can be coupled together with a suitable data communication network so as to collectively perform the various functions, methods, or operations disclosed herein.

A number of embodiments have been described. Nevertheless, it will be understood that various modifications may be made without departing from the spirit and scope of the invention.

In addition, the logic flows depicted in the figures do not require the particular order shown, or sequential order, to achieve desirable results. In addition, other steps may be provided, or steps may be eliminated, from the described flows, and other components may be added to, or removed from, the described systems.

While certain features of the described implementations have been illustrated as described herein, many modifications, substitutions, changes and equivalents will now occur to those skilled in the art. It is, therefore, to be understood that appended claims are intended to cover all such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components and/or features of the different implementations described.

What is claimed is:

1. A method of adjusting insulin therapy settings of a portable drug delivery device for a person with diabetes that treats the diabetes by administering first and second types of insulin, the method comprising:

storing, in a non-transitory storage medium of the portable drug delivery device, a first-type insulin dosage suggestion for a person with diabetes regarding a first type of insulin having an active time that is longer than an active time for a second type of insulin;

receiving, via a communication link between a blood glucose sensor and a processor of the portable drug delivery device, blood glucose data obtained by the blood glucose sensor for the person with diabetes, the blood glucose data including blood glucose values for a plurality of days;

determining, by the processor of the portable drug delivery device, a first variability of the blood glucose values for a first period of time during the plurality of days, wherein the first period of time includes multiple time segments from the plurality of days that correspond to each other, each time segment beginning a predefined elapsed time after a second type of insulin dosage time;

modifying, by the processor of the portable drug delivery device, the first-type insulin dosage suggestion in the non-transitory storage medium using only the determined first variability; and administering the first type of insulin to the person with diabetes using the portable drug delivery device according to the modified first-type according to the modified first-type insulin dosage suggestion.

2. The method of claim 1, further comprising:

storing, in the non-transitory storage medium, a second-type insulin dosage suggestion for the person with diabetes regarding the second type of insulin;

receiving second-type insulin dosage times for the person with diabetes regarding the plurality of days;

determining a second variability of the blood glucose values for a second period of time during the plurality of days, the second period of time not overlapping the first period of time; and modifying the second-type insulin dosage suggestion in the non-transitory storage medium based on the determined second variability.

3. The method of claim 1, wherein determining the first variability comprises determining a measure of dispersion for the blood glucose values for the first period of time.

4. The method of claim 3, wherein determining the measure of dispersion comprises determining a percentage of the blood glucose values for the first period of time that fall below a threshold blood glucose level.

5. The method of claim 4, wherein modifying the first-type insulin dosage suggestion comprises:

in response to the percentage exceeding a threshold percentage, decreasing the first-type insulin dosage suggestion; and in response to the percentage being less than the threshold percentage, increasing the first-type insulin dosage suggestion.

6. The method of claim 3, wherein determining the measure of dispersion comprises evaluating a logarithm-based cost function for the blood glucose values as measured for the first period of time.

7. The method of claim 3, wherein determining the measure of dispersion comprises determining an area-under-the-curve value for the blood glucose values for the first period of time, the area-under-the-curve value determined based on a threshold blood glucose value, wherein the blood glucose values during the first period of time correspond to a fasting time or sleeping time for the person with diabetes.

8. The method of claim 3, wherein determining the measure of dispersion includes evaluating a mean value of a distribution of the blood glucose values for the first period of time, and a standard deviation of the distribution of the blood glucose values for the first period of time.

9. The method of claim 3, wherein determining the measure of dispersion comprises comparing the predefined mean value to the mean value with a buffer value added to the mean value, and comparing the predefined mean value to the mean value with the buffer value subtracted from the mean value, wherein the buffer value is derived from an insulin sensitivity factor of the person with diabetes and a minimum dose change amount.

10. The method of claim 1, further comprising determining the second-type of insulin dosage time by monitoring a cap sensor of a pen cap, the pen cap including a communications subsystem for enabling wireless communication between the pen cap and processor, wherein the pen cap is configured to removably fit over and cap at least a portion of an insulin injection pen, and the cap sensor detects physical removal of the pen cap from the insulin injection pen and generates a removal signal and the determining of the second-type of insulin dosage time is based on the removal signal.

11. The method of claim 1, wherein the first period of time is selected as being at least one of fasting time or sleeping time for the person with diabetes.

12. A method of adjusting insulin therapy settings for a person with diabetes that treats the diabetes by administering first and second types of insulin via a portable drug delivery device, the method comprising:

storing, in a non-transitory storage medium of the portable drug delivery device, a second-type insulin dosage suggestion for a person with diabetes regarding a second type of insulin having an active time that is shorter than an active time for a first type of insulin;

receiving, via a communication link between a blood glucose sensor and the portable drug delivery device, blood glucose data for the person with diabetes, the blood glucose data including blood glucose values for a plurality of days;

receiving, by a processor of the portable drug delivery device, second-type insulin dosage times for the person with diabetes regarding the plurality of days;

determining, by the processor of the portable drug delivery device, a first variability of the blood glucose values for a selected first period of time during the plurality of days based on a selected metric, wherein the selected first period of time includes multiple time segments from the plurality of days that correspond to each other, each time segment beginning a predefined elapsed time after a second type of insulin dosage time during a respective day of the plurality of days;

modifying the second-type insulin dosage suggestion in the non-transitory storage medium based on only the determined first variability; and administering to a person with diabetes, via the portable drug delivery device, the second type of insulin according to the modified second-type insulin dosage suggestion.

13. The method of claim 12, wherein determining the first variability comprises determining a measure of dispersion for the blood glucose values for the selected first period of time.

14. The method of claim 12, further comprising:

storing, in the non-transitory storage medium, a first-type insulin dosage suggestion for the person with diabetes regarding the first type of insulin;

determining a measure of dispersion for the blood glucose values for the selected second period of time during the plurality of days, the second period of time not overlapping the first period of time; and modifying the first-type insulin dosage suggestion in the non-transitory storage medium based on the determined measure of dispersion.

15. The method of claim 14, wherein the selected second period of time is selected as beginning after a third period of time following a first-type of insulin dosage time during the plurality of days.

16. A portable diabetes management device comprising:

a processor; and a non-transitory storage medium having stored therein:

a first-type insulin dosage suggestion for a person with diabetes regarding a first type of insulin having an active time that is longer than an active time for a second type of insulin;

blood glucose data for the person with diabetes, the blood glucose data including blood glucose values for a plurality of days; and instructions that when executed cause the processor to:

determine a first variability of the blood glucose values for a first period of time during the plurality of days, wherein the first period of time includes multiple time segments from the plurality of days that correspond to each other, each time segment beginning a predefined elapsed time after a second type of insulin dosage time during a respective day of the plurality of days;

assess a first-type insulin dosage suggestion stored in the non-transitory storage medium with respect to only the determined first variability;

modify the first-type insulin dosage suggestion stored in the non-transitory storage medium based on the assessment of the first variability indicating the first-type insulin dosage suggestion led to an undesirable blood glucose level; and administer to the person with diabetes, via an insulin injection pen of the portable diabetes management device, the first-type insulin based on the modified first-type insulin dosage suggestion.

17. The portable diabetes management device of claim 16, wherein the diabetes management device is a pen cap having a processor and configured to removably fit over and cap at least a portion of an insulin injection pen, and the pen cap comprising a cap sensor operable to detect physical removal of the pen cap and generate a signal indicative of the physical removal of the pen cap from the insulin injection pen.

18. The portable diabetes management device of claim 17, wherein the processor of the pen cap is further operable to:

monitor communications from the cap sensor regarding signals indicating the physical removal of the pen cap from the insulin injection pen;

determine a time of the physical removal of the pen cap from the insulin injection pen; and determine the second-type of insulin dosage time based on the determined time of the physical removal of the pen cap, wherein the second-type of insulin dosage time is used as an input to the variability determination for the selected first period of time.

19. The portable diabetes management device of claim 16, wherein the diabetes management device is a continuous glucose monitor.

* * * * *